(12) United States Patent
Bencsik et al.

(10) Patent No.: US 8,846,683 B2
(45) Date of Patent: Sep. 30, 2014

(54) PYRIMIDYL CYCLOPENTANES AS AKT PROTEIN KINASE INHIBITORS

(71) Applicants: Array BioPharma Inc., Boulder, CO (US); Genentech, Inc., South San Francisco, CA (US)

(72) Inventors: Josef R. Bencsik, Boulder, CO (US); James F. Blake, Boulder, CO (US); Nicholas C. Kallan, Boulder, CO (US); Ian S. Mitchell, Boulder, CO (US); Keith L. Spencer, Boulder, CO (US); Dengming Xiao, Boulder, CO (US); Rui Xu, Boulder, CO (US); Christine Chabot, South San Francisco, CA (US); Jun Liang, South San Francisco, CA (US); Brian S. Safina, South San Francisco, CA (US)

(73) Assignees: Array BioPharma, Inc., Boulder, CO (US); Genentech, Inc., South San Francisco, CA (US)

( * ) Notice: Subject to any disclaimer, the term of this patent is extended or adjusted under 35 U.S.C. 154(b) by 0 days.

(21) Appl. No.: 13/753,008

(22) Filed: Jan. 29, 2013

(65) Prior Publication Data

US 2013/0143865 A1 Jun. 6, 2013

Related U.S. Application Data

(63) Continuation of application No. 12/667,850, filed as application No. PCT/US2008/069147 on Jul. 3, 2008, now Pat. No. 8,377,937.

(60) Provisional application No. 60/948,147, filed on Jul. 5, 2007.

(51) Int. Cl.
*A61P 35/00* (2006.01)

(52) U.S. Cl.
USPC .................................................. 514/252.16

(58) Field of Classification Search
USPC .................................................. 514/252.16
See application file for complete search history.

(56) References Cited

U.S. PATENT DOCUMENTS

| | | | |
|---|---|---|---|
| 3,885,035 A | 5/1975 | Simpson | |
| 3,956,495 A | 5/1976 | Lacefield | |
| 3,966,936 A | 6/1976 | Cronin et al. | |
| 4,060,615 A | 11/1977 | Matier et al. | |
| 4,352,928 A | 10/1982 | Hiranuma et al. | |
| 5,051,412 A | 9/1991 | Macor | |
| 5,525,625 A | 6/1996 | Bridges et al. | |
| 5,563,152 A | 10/1996 | Kulagowski et al. | |
| 5,610,303 A | 3/1997 | Kimura et al. | |
| 5,750,531 A | 5/1998 | Lee et al. | |
| 5,750,545 A | 5/1998 | Akahoshi et al. | |
| 5,817,671 A | 10/1998 | Filla et al. | |
| 6,310,060 B1 | 10/2001 | Barrett et al. | |
| 6,423,716 B1 | 7/2002 | Matsuno et al. | |
| 6,469,004 B1 | 10/2002 | Barrett et al. | |
| 6,506,798 B1 | 1/2003 | Barrett et al. | |
| 6,627,628 B1 | 9/2003 | Schindler et al. | |
| 6,831,175 B2 | 12/2004 | Li et al. | |
| 7,041,687 B2 | 5/2006 | Binch et al. | |
| 7,067,664 B1 | 6/2006 | Chen | |
| 7,115,741 B2 | 10/2006 | Levy et al. | |
| 7,125,880 B1 | 10/2006 | Chen | |
| 7,223,738 B2 | 5/2007 | Bilodeau et al. | |
| 7,223,767 B2 | 5/2007 | Clark et al. | |
| 8,003,651 B2 | 8/2011 | Mitchell et al. | |
| 8,063,050 B2 | 11/2011 | Mitchell et al. | |
| 8,329,701 B2 | 12/2012 | Mitchell et al. | |
| 8,329,709 B2 | 12/2012 | Banka et al. | |
| 8,377,937 B2 | 2/2013 | Bencsik et al. | |
| 2003/0004193 A1 | 1/2003 | Barrett et al. | |

(Continued)

FOREIGN PATENT DOCUMENTS

| | | |
|---|---|---|
| EP | 194161 A2 | 9/1986 |
| JP | 2004-512277 | 4/2004 |

(Continued)

OTHER PUBLICATIONS

Bellacosa et al., "Molecular alterations of the AKT2 oncogene in ovarian and breast carcinomas", Int. J. Cancer 64(4), 280-285 (1995).
Bhaskar et al., "The PI3K-Akt-mTOR pathway regulates Aβ oligomer induced neuronal cell cycle events", *Molecular Neurodegeneration*, 4, 14, 18 pages (2009).
Brognard et al., "Akt/Protein Kinase B is Constitutively Active in Non-Small Cell Lung Cancer Cells and Promotes Cellular Survival and Resistance to Chemotherapy and Radiation", *Cancer Res.* 61, 3986-3997 (2001).

(Continued)

*Primary Examiner* — Bruck Kifle
(74) *Attorney, Agent, or Firm* — Viksnins Harris & Padys PLLP

(57) ABSTRACT

The present invention provides compounds of Formula I, including tautomers, resolved enantiomers, diastereomers, solvates, metabolites, salts and pharmaceutically acceptable prodrugs thereof.

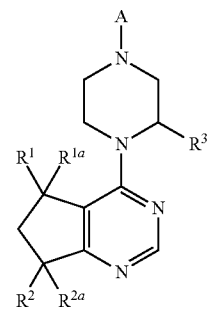

Also provided are methods of using the compounds of this invention as AKT protein kinase inhibitors and for the treatment of hyperproliferative diseases such as cancer.

35 Claims, No Drawings

(56) References Cited

U.S. PATENT DOCUMENTS

| | | |
|---|---|---|
| 2003/0045521 A1 | 3/2003 | Tecle |
| 2003/0078428 A1 | 4/2003 | Barrett et al. |
| 2003/0092748 A1 | 5/2003 | Barrett et al. |
| 2003/0199511 A1 | 10/2003 | Lee et al. |
| 2003/0216460 A1 | 11/2003 | Wallace et al. |
| 2003/0232869 A1 | 12/2003 | Wallace et al. |
| 2004/0053933 A1 | 3/2004 | Pontillo et al. |
| 2004/0102360 A1 | 5/2004 | Barnett et al. |
| 2004/0116710 A1 | 6/2004 | Wallace et al. |
| 2004/0176400 A1 | 9/2004 | Capelli et al. |
| 2005/0059687 A1 | 3/2005 | Makings et al. |
| 2005/0130954 A1 | 6/2005 | Mitchell et al. |
| 2005/0182061 A1 | 8/2005 | Green et al. |
| 2007/0004708 A1 | 1/2007 | Andreotti et al. |
| 2007/0027156 A1 | 2/2007 | Nakai et al. |
| 2007/0135466 A1 | 6/2007 | Ledeboer et al. |
| 2008/0051399 A1 | 2/2008 | Mitchell et al. |
| 2008/0076774 A1 | 3/2008 | Anand et al. |
| 2008/0188482 A1 | 8/2008 | Rice et al. |
| 2010/0168123 A1 | 7/2010 | Mitchell et al. |
| 2010/0292244 A1 | 11/2010 | Bencsik et al. |
| 2011/0015204 A1 | 1/2011 | Bencsik et al. |
| 2011/0065716 A1 | 3/2011 | Bencsik et al. |
| 2011/0245230 A1 | 10/2011 | Mitchell et al. |
| 2012/0232055 A1 | 9/2012 | Mitchell et al. |
| 2012/0329808 A1 | 12/2012 | Mitchell et al. |
| 2013/0065908 A1 | 3/2013 | Mitchell et al. |
| 2013/0085135 A1 | 4/2013 | Banka et al. |

FOREIGN PATENT DOCUMENTS

| | | |
|---|---|---|
| JP | 2007-512364 | 5/2007 |
| WO | WO 95/03286 A1 | 2/1995 |
| WO | WO 98/43960 A1 | 10/1998 |
| WO | WO 99/01421 A1 | 1/1999 |
| WO | WO 99/01426 A1 | 1/1999 |
| WO | WO 00/40235 A2 | 7/2000 |
| WO | WO 00/40237 A1 | 7/2000 |
| WO | WO 00/41505 A2 | 7/2000 |
| WO | WO 00/41994 A1 | 7/2000 |
| WO | WO 00/42002 A1 | 7/2000 |
| WO | WO 00/42003 A1 | 7/2000 |
| WO | WO 00/42022 A1 | 7/2000 |
| WO | WO 00/42029 A1 | 7/2000 |
| WO | WO 00/68201 A1 | 11/2000 |
| WO | WO 01/05390 A2 | 1/2001 |
| WO | WO 01/05391 A2 | 1/2001 |
| WO | WO 01/05392 A2 | 1/2001 |
| WO | WO 01/05393 A2 | 1/2001 |
| WO | WO 01/68619 A1 | 9/2001 |
| WO | WO 02/06213 A2 | 1/2002 |
| WO | WO 02/18319 A1 | 3/2002 |
| WO | WO 02/22604 A1 | 3/2002 |
| WO | WO 02/44166 A1 | 6/2002 |
| WO | WO 02/083139 A1 | 10/2002 |
| WO | WO 03/022214 A2 | 3/2003 |
| WO | WO 03/064397 A1 | 8/2003 |
| WO | WO 03/077855 A2 | 9/2003 |
| WO | WO 03/077914 A1 | 9/2003 |
| WO | WO 03/086279 A2 | 10/2003 |
| WO | WO 03/086394 A1 | 10/2003 |
| WO | WO 03/086403 A1 | 10/2003 |
| WO | WO 03/086404 A1 | 10/2003 |
| WO | WO 03/094918 A1 | 11/2003 |
| WO | WO 2004/041162 A2 | 5/2004 |
| WO | WO 2004/096130 A2 | 11/2004 |
| WO | WO 2005/014558 A1 | 2/2005 |
| WO | WO 2005/051304 A2 | 6/2005 |
| WO | WO 2005/117909 A2 | 12/2005 |
| WO | WO 2006/046023 A1 | 5/2006 |
| WO | WO 2006/071819 A1 | 7/2006 |
| WO | WO 2006/090261 A1 | 8/2006 |
| WO | WO 2006/136830 A1 | 12/2006 |
| WO | WO 2007/042298 A1 | 4/2007 |
| WO | WO 2007/077961 A2 | 7/2007 |
| WO | WO 2007/125320 A1 | 11/2007 |
| WO | WO 2008/003697 A1 | 1/2008 |
| WO | WO 2008/003958 A2 | 1/2008 |
| WO | WO 2008/003978 A2 | 1/2008 |
| WO | WO 2008/005511 A2 | 1/2008 |
| WO | WO 2008/005964 A2 | 1/2008 |
| WO | WO 2008/006032 A1 | 1/2008 |
| WO | WO 2008/006040 A1 | 1/2008 |
| WO | WO 2008/012635 A2 | 1/2008 |

OTHER PUBLICATIONS

Di Lorenzo et al., "Akt1 is critical for acute inflammation and histamine-mediated vascular leakage", *PNAS*, vol. 106(34), 14552-14557 (2009).

Cheng et al., "AKT2, a putative oncogene encoding a member of a subfamily of protein-serine/threonine kinases, is amplifeed in human ovarian carcinomas", *Proc. Natl., Acad. Sci.*, 89, 9267-9271 (1992).

Cheng et al., "Amplification of AKT2 in human pancreatic cancer cells and inhibition of AKT2 expression and tumorigenicity by antisense RNA", *Proc. Natl. Acad. Sci*, 93, 3636-3641 (1996).

Entsiklopediya lekarstv [Drug Encyclopedia] RLS-2007, Moscow, col. 2, section "Characterization", p. 1032-1033, (2006).

Graff et al., "Increased AKT Activity Contributes to Prostate Cancer Progression by Dramatically Accelerating Prostate Tumor Growth and Diminishing $p27^{Kip1}$ Expression", *J. Biol. Chem.*, 275(32), 24500-24505 (2000).

Haas Kogan et al., "Protein kinase B (PKB/Akt) activity is elevated in glioblastoma cells due to mutation of the tumor suppressor PTEN/MMAC", *Curr. Biol.*, 8, 1195-1198 (1998).

Li, Q., "Recent progress in the discovery of Akt inhibitors as anticancer agents", *Expert Opinion: Informa Healthcare* 17(9), pp. 1077-1130, 2007.

Ohno, S. et al., "Synthesis and Hypoglycemic Activity of 7,8-Dihydro-6H-thiopyrano[3,2-d]pyrimidine Derivatives and Related Compounds", *Chem. Pharm. Bull.* 34(10), pp. 4150-4165, 1986.

Patent Cooperation Treaty, International Search Report and Written Opinion of the International Searching Authority, PCT/US2008/069147, 13 pages, Nov. 10, 2008.

Rajaram et al., "Akt/Protein Kinase B Modulates Macrophage Inflammatory Response to *Francisella* Infection and Confers a Survival Advantage in Mice", *The Journal of Immunology*, 177, 6317-6324 (2006).

Ross, L.O. et al., "Potential Anticancer Agents. XVIII. Synthesis of Substituted 4,5-Trimethylenepyrimidines", *J.Am. Chem. Soc.*, vol. 81, pp. 3108-3113, 1959.

Russian Office Action for RU Application No. 2010103811, including translation, 11 pages, May 30, 2012.

Staal, "Molecular cloning of the akt oncogene and its human homologues AKT1 and AKT2: Amplification of AKT1 in a primary human gastric adenocarcinoma", *Proc. Natl. Acad. Sci.*, 84, 5034-5037 (1987).

Office Action and translation thereof issued by the Japanese Patent Office in corresponding Application No. 2010-515269, Jun. 4, 2013 (mailing date), 7 pages.

Toker et al., "Akt Signaling and Cancer: Surviving but not Moving on", *Cancer Res.*, 66(8), 3963-3966 (2006).

Tyukavkina et al., Bioorganicheskaya khimiya [Bioorganic Chemistry], $4^{th}$ Edition, "Drofa", Moscow, pp. 83-85, (2005).

Vippagunta, S.R., *Advanced Drug Delivery Reviews*, vol. 48, pp. 3-26, 2001.

Zhao, Z. et al., "Discovery of 2,3,5-trisubstituted pyridine derivatives as potent Akt1 and Akt2 dual inhibitors", *Bioorganic & Medicinal Chemistry Letters*, vol. 15, pp. 905-909, 2005.

Zinda et al., "Akt-1, -2, and -3 are Expressed in Both Normal and Tumor Tissues of the Lung, Breast, Prostate, and Colon", *Clin. Cancer Res.*, 7, 2475-2479 (2001).

US 8,846,683 B2

PYRIMIDYL CYCLOPENTANES AS AKT PROTEIN KINASE INHIBITORS

PRIORITY OF INVENTION

This application is a continuation of U.S. patent application Ser. No. 12/667,850, which is a 35 U.S.C. 371 national stage application of International Patent Application No. PCT/US2008/069147, filed Jul. 3, 2008, and claims priority to U.S. Provisional Application No. 60/948,147, filed Jul. 5, 2007, which are hereby incorporated herein by reference in their entirety.

BACKGROUND OF THE INVENTION

1. Field of the Invention

This invention relates to novel inhibitors of serine/threonine protein kinases (e.g., AKT and related kinases), pharmaceutical compositions containing the inhibitors, and methods for preparing these inhibitors. The inhibitors are useful, for example, for the treatment of hyperproliferative diseases, such as cancer and inflammation, in mammals.

2. Description of the State of the Art

Protein kinases (PK) are enzymes that catalyze the phosphorylation of hydroxy groups on tyrosine, serine and threonine residues of proteins by transfer of the terminal (gamma) phosphate from ATP. Through signal transduction pathways, these enzymes modulate cell growth, differentiation and proliferation, i.e., virtually all aspects of cell life in one way or another depend on PK activity (Hardie, G. and Hanks, S. (1995) *The Protein Kinase Facts Book I and II*, Academic Press, San Diego, Calif.). Furthermore, abnormal PK activity has been related to a host of disorders, ranging from relatively non-life threatening diseases, such as psoriasis, to extremely virulent diseases, such as glioblastoma (brain cancer). Protein kinases are an important target class for therapeutic modulation (Cohen, P. (2002) Nature Rev. Drug Discovery 1:309).

Significantly, atypical protein phosphorylation and/or expression is often reported to be one of the causative effects of abnormal cellular proliferation, metastasis and cell survival in cancer. The abnormal regulation and/or expression of various kinases, including Akt, VEGF, ILK, ROCK, p70S6K, Bcl, PKA, PKC, Raf, Src, PDK1, ErbB2, MEK, IKK, Cdk, EGFR, BAD, CHK1, CHK2 and GSK3 amongst numerous others, has been specifically implicated in cancer.

Protein kinases include two classes; protein tyrosine kinases (PTK) and serine-threonine kinases (STK). The Protein Kinase B/Akt enzymes are a group of serine/threonine kinases that are overexpressed in a variety of human tumors. One of the best-characterized targets of the PI3K lipid products is the 57 KD serine/threonine protein kinase Akt, downstream of PI3K in the signal transduction pathway (Hemmings, B. A. (1997) Science 275:628; Hay N. (2005) Cancer Cell 8:179-183). Akt is the human homologue of the protooncogene v-akt of the acutely transforming retrovirus AKT8. Due to its high sequence homology to protein kinases A and C, Akt is also called Protein Kinase B (PKB) and Related to A and C(RAC). Three isoforms of Akt are known to exist, namely Akt1, Akt2 and Akt3, which exhibit an overall homology of 80% (Staal, S. P. (1987) Proc. Natl. Acad. Sci. 84:5034; Nakatani, K. (1999) Biochem. Biophys. Res. Commun. 257:906; Li et al (2002) Current Topics in Med. Chem. 2:939-971; WO 2005/113762). The Akt isoforms share a common domain organization that consists of a pleckstrin homology domain at the N-terminus, a kinase catalytic domain, and a short regulatory region at the C-terminus. In addition, both Akt2 and Akt3 exhibit splice variants. Upon recruitment to the cell membrane by PtdInd(3,4,5)P$_3$, Akt is phosphorylated (activated) by PDK1 at T308, T309 and T305 for isoforms Akt1 (PKBα), Akt2 (PKBβ) and Akt3 (PKBγ), respectively, and at S473, S474 and S472 for isoforms Akt1, Akt2 and Akt3, respectively. Such phosphorylation occurs by an as yet unknown kinase (putatively named PDK2), although PDK1 (Balendran, A., (1999) Curr. Biol. 9:393), autophosphorylation (Toker, A. (2000) J. Biol. Chem. 275:8271) and integrin-linked kinase (ILK) (Delcommenne, M. (1998) Proc. Natl. Acad. Sci. USA, 95:11211) have been implicated in this process. Akt activation requires its phosphorylation on residue Ser 473 in the C-terminal hydrophobic motif (Brodbeck et al (1999) J. Biol. Chem. 274:9133-9136; Coffer et al (1991) Eur. J. Biochem. 201:475-481; Alessi et al (1997) Curr. Biol. 7:261-269). Although monophosphorylation of Akt activates the kinase, bis(phosphorylation) is required for maximal kinase activity.

Akt is believed to assert its effect on cancer by suppressing apoptosis and enhancing both angiogenesis and proliferation (Toker et al (2006) Cancer Res. 66(8):3963-3966). Akt is overexpressed in many forms of human cancer including, but not limited to, colon (Zinda et al (2001) Clin. Cancer Res. 7:2475), ovarian (Cheng et al (1992) Proc. Natl. Acad. Sci. USA 89:9267), brain (Haas Kogan et al (1998) Curr. Biol. 8:1195), lung (Brognard et al (2001) Cancer Res. 61:3986), pancreatic (Bellacosa et al (1995) Int. J. Cancer 64:280-285; Cheng et al (1996) Proc. Natl. Acad. Sci. 93:3636-3641), prostate (Graff et al (2000) J. Biol. Chem. 275:24500) and gastric carcinomas (Staal et al (1987) Proc. Natl. Acad. Sci. USA 84:5034-5037).

The PI3K/Akt/mammalian target of rapamycin (mTOR) pathway has been explored for targeted small molecule inhibitor therapy (Georgakis, G. and Younes, A. (2006) Expert Rev. Anticancer Ther. 6(1):131-140; Granville et al (2006) Clin. Cancer Res. 12(3):679-689). Inhibition of PI3K/Akt signaling induces apoptosis and inhibits the growth of tumor cells that have elevated Akt levels (Kim et al (2005) Current Opinion in Investig. Drugs 6(12):1250-1258; Luo et al (2005) Molecular Cancer Ther. 4(6):977-986).

The development of kinase inhibitors that target abnormally regulated pathways and ultimately result in disease is of enormous ethical and commercial interest to the medical and pharmaceutical community. A compound that inhibits (1) recruitment of Akt to the cell membrane, (2) activation by PDK1 or PDK2, (3) substrate phosphorylation, or (4) one of the downstream targets of Akt could be a valuable anticancer agent, either as a stand-alone therapy or in conjunction with other accepted procedures.

United States Patent Application Publication 2005/0130954 discloses inter alia, a variety of compounds that act as AKT inhibitors. The compounds are said to be useful in the treatment of hyperproliferative diseases such as cancer.

United States Patent Application Publication 2008/0058327 and United States Patent Application Publication 2008/0051399 disclose inter alia, a variety of compounds that act as AKT inhibitors.

SUMMARY OF THE INVENTION

This invention provides novel compounds that inhibit AKT protein kinases. The compounds of the present invention have utility as therapeutic agents for diseases and conditions that can be treated by the inhibition of AKT protein kinases.

The present invention includes compounds having the general Formula I:

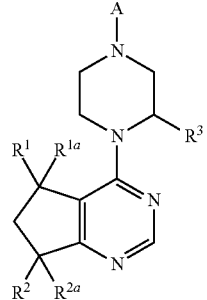

and enantiomers and salts thereof, wherein A, $R^1$, $R^{1a}$, $R^2$, $R^{2a}$, and $R^3$ are as defined below.

The invention also provides pharmaceutical compositions comprising a compound of Formula I, or an enantiomer or pharmaceutically acceptable salt thereof.

In a further aspect, the present invention provides a method of treating diseases or medical conditions in a mammal mediated by AKT protein kinases, comprising administering to said mammal one or more compounds of Formula I, or an enantiomer or pharmaceutically acceptable salt thereof, in an amount effective to treat or prevent said disorder. AKT protein kinase mediated conditions that can be treated according to the methods of this invention include, but are not limited to, inflammatory, hyperproliferative, cardiovascular, neurodegenerative, gynecological, and dermatological diseases and disorders.

In a further aspect, the present invention provides a method of inhibiting the production of AKT protein kinases in a mammal, which comprises administering to said mammal a compound of Formula I, or an enantiomer or pharmaceutically acceptable salt thereof in an amount effective to inhibit production of an AKT protein kinase.

In a further aspect, the present invention provides methods of inhibiting the activity of AKT protein kinases, comprising contacting said kinase with a compound of Formula I.

The inventive compounds may be used advantageously in combination with other known therapeutic agents. Accordingly, this invention also provides pharmaceutical compositions comprising a compound of Formula I or an enantiomer or pharmaceutically acceptable salt thereof, in combination with a second therapeutic agent.

This invention also provides compounds of Formula I and enantiomers and pharmaceutically acceptable salts thereof for use as medicaments in the treatment of AKT protein kinase-mediated conditions.

An additional aspect of the invention is the use of a compound of Formula I, or an enantiomer or pharmaceutically acceptable salt thereof, for therapy. In one embodiment, the therapy comprises the treatment of an AKT protein kinase-mediated condition.

This invention further provides kits for the treatment of an AKT protein kinase-mediated disease or disorder, said kit comprising a compound of Formula I, or an enantiomer or pharmaceutically acceptable salt thereof, a container, and optionally a package insert or label indicating a treatment. The kits may further comprise a second compound or formulation comprising a second pharmaceutical agent useful for treating said disease or disorder.

This invention further includes methods of preparing, methods of separating, and methods of purifying of the compounds of this invention.

Additional advantages and novel features of this invention shall be set forth in part in the description that follows, and in part will become apparent to those skilled in the art upon examination of the following specification, or may be learned by the practice of the invention. The advantages of the invention may be realized and attained by means of the instrumentalities, combinations, compositions, and methods particularly pointed out in the appended claims.

DETAILED DESCRIPTION OF THE INVENTION

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature and similar materials differs from or contradicts this application, including but not limited to defined terms, term usage, described techniques, or the like, this application controls.

Definitions

The term "alkyl" as used herein refers to a saturated linear or branched-chain monovalent hydrocarbon radical of one to twelve carbon atoms, wherein the alkyl radical may be optionally substituted independently with one or more substituents described below. Examples of alkyl groups include, but are not limited to, methyl ("Me", —$CH_3$), ethyl ("Et", —$CH_2CH_3$), 1-propyl ("n-Pr", n-propyl, —$CH_2CH_2CH_3$), 2-propyl ("i-Pr", i-propyl, —$CH(CH_3)_2$), 1-butyl ("n-Bu", n-butyl, —$CH_2CH_2CH_2CH_3$), 2-methyl-1-propyl ("i-Bu", i-butyl, —$CH_2CH(CH_3)_2$), 2-butyl ("s-Bu", s-butyl, —$CH(CH_3)CH_2CH_3$), 2-methyl-2-propyl ("t-Bu", t-butyl, tert-butyl, —$C(CH_3)_3$), 2,2-dimethylpropyl ($CH_2C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), 1-heptyl, 1-octyl, and the like.

The terms "cycloalkyl," "carbocycle," "carbocyclyl" and "carbocyclic ring" as used herein are used interchangeably and refer to saturated or partially unsaturated cyclic hydrocarbon radical having from three to twelve carbon atoms. The term "cycloalkyl" includes monocyclic and polycyclic (e.g., bicyclic and tricyclic) cycloalkyl structures, wherein the polycyclic structures optionally include a saturated or partially unsaturated cycloalkyl ring fused to a saturated, partially unsaturated or aromatic cycloalkyl or heterocyclic ring. The cycloalkyl may be optionally substituted independently with one or more substituents described herein.

Examples of cycloalkyl groups include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, bicyclo[2.2.1]heptane, bicyclo[2.2.2]octane, and bicyclo[3.2.2]nonane.

The terms "heterocycle", "heterocyclyl" and "heterocyclic ring" as used herein are used interchangeably and refer to a saturated or partially unsaturated carbocyclic radical of 3 to 8 ring atoms in which at least one ring atom is a heteroatom independently selected from nitrogen, oxygen and sulfur, the remaining ring atoms being C, where one or more ring atoms may be optionally substituted independently with one or more substituents described below. The radical may be a carbon radical or heteroatom radical. The term "heterocycle" includes heterocycloalkoxy. "Heterocyclyl" also includes radicals where heterocycle radicals are fused with a saturated, partially unsaturated, or aromatic carbocyclic or heterocyclic ring. The heterocycle may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached). Examples of heterocyclic groups wherein 2 ring carbon atoms are substituted with oxo (=O) moieties are isoindoline-1,3-dionyl and 1,1-dioxo-thiomorpholinyl. The heterocycle groups herein are optionally substituted independently with one or more substituents described herein.

Exemplary heterocyclyl groups include, but are not limited to, oxiranyl, aziridinyl, thiiranyl, azetidinyl, oxetanyl, thietanyl, 1,2-dithietanyl, 1,3-dithietanyl, pyrrolidinyl, piperidinyl, morpholinyl, thiomorpholinyl, thioxanyl, piperazinyl, homopiperazinyl, homopiperidinyl, oxepanyl, thiepanyl, oxazepinyl, diazepinyl, thiazepinyl, dihydrothienyl, dihydropyranyl, dihydrofuranyl, tetrahydrofuranyl, tetrahydrothienyl, tetrahydropyranyl, tetrahydrothiopyranyl, 1-pyrrolinyl, 2-pyrrolinyl, 3-pyrrolinyl, indolinyl, 2H-pyranyl, 4H-pyranyl, dioxanyl, 1,3-dioxolanyl, pyrazolinyl, pyrazolidinyl, dithianyl, dithiolanyl, pyrazolidinylimidazolinyl, imidazolidinyl, 3-azabicyco[3.1.0]hexanyl, 3-azabicyclo[4.1.0]heptanyl and azabicyclo[2.2.2]hexanyl.

The term "heteroaryl" as used herein refers to a monovalent aromatic radical of a 5-, 6-, or 7-membered ring and includes fused ring systems (at least one of which is aromatic) of 5-10 atoms containing at least one heteroatom independently selected from nitrogen, oxygen, and sulfur. The heteroaryl may be C-attached or N-attached where such is possible. Heteroaryl groups may be optionally substituted independently with one or more substituents described herein.

Examples of heteroaryl groups include, but are not limited to, pyridinyl, imidazolyl, imidazopyridinyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

The term "halogen" as used herein means fluoro, chloro, bromo or iodo.

The term "enantiomer" refers to two stereoisomers of a compound which are non-superimposable mirror images of one another.

The term "diastereomer" refers to a pair of optical isomers which are not mirror images of one another.

The term "tautomer" or "tautomeric form" refers to structural isomers of different energies which are interconvertible via a low energy barrier.

The phrase "pharmaceutically acceptable" indicates that the substance or composition is compatible chemically and/or toxicologically with the other ingredients comprising a formulation, and/or the mammal being treated therewith.

The phrase "effective amount" means an amount of compound that, when administered to a mammal in need of such treatment, is sufficient to (i) treat or prevent a particular disease, condition, or disorder mediated by the activity of one or more AKT protein kinases, tyrosine kinases, additional serine/threonine kinases, and/or dual specificity kinases, (ii) attenuate, ameliorate, or eliminate one or more symptoms of the particular disease, condition, or disorder, or (iii) prevent or delay the onset of one or more symptoms of the particular disease, condition, or disorder described herein.

"Treating" is intended to mean at least the mitigation of a disease condition in a mammal, such as a human, that is affected, at least in part, by the activity of one or more AKT protein kinases, tyrosine kinases, additional serine/threonine kinases, and/or dual specificity kinases. The terms "treat" and "treatment" refer to both therapeutic treatment and prophylactic or preventative measures, wherein the object is to prevent or slow down (lessen) an undesired physiological change or disorder. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those found to be predisposed to having the disease condition but have not yet been diagnosed as having it; modulating and/or inhibiting the disease condition. The terms "treating", "treat", or "treatment" embrace both preventative, i.e., prophylactic, and palliative treatment.

As used herein, the term "mammal" refers to a warm-blooded animal that has or is at risk of developing a disease described herein and includes, but is not limited to, guinea pigs, dogs, cats, rats, mice, hamsters, and primates, including humans.

The term "package insert" is used to refer to instructions customarily included in commercial packages of therapeutic products, that contain information about the indications, usage, dosage, administration, contraindications and/or warnings concerning the use of such therapeutic products.

The term "a" as used herein means one or more.

As used herein, the terms "compound of this invention," "compounds of the present invention" and "compounds of Formula I" includes compounds of Formula I and tautomers, resolved enantiomers, resolved diastereomers, racemic mixtures, solvates, metabolites, salts (including pharmaceutically acceptable salts) and pharmaceutically acceptable prodrugs thereof.

It is to be understood that in instances where two or more radicals are used in succession to define a substituent attached to a structure, the first named radical is considered to be terminal and the last named radical is considered to be attached to the structure in question. Thus, for example, an arylalkyl radical is attached to the structure in question by the alkyl group.

AKT Inhibitors

The inventive compounds of Formula I are useful for inhibiting AKT protein kinases. The compounds of Formula I may also be useful as inhibitors of tyrosine kinases as well as serine and threonine kinases in addition to AKT. Such compounds have utility as therapeutic agents for diseases that can be treated by the inhibition of the AKT protein kinase signaling pathway and tyrosine and serine/threonine kinase receptor pathways.

In general, the invention includes compounds of the Formula I:

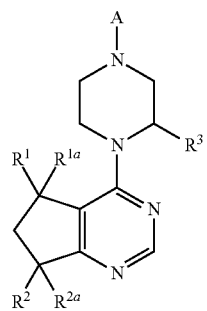

I and resolved enantiomers, resolved diastereomers, and pharmaceutically acceptable salts thereof, wherein:

$R^1$ and $R^{1a}$ are independently selected from H, Me, Et, vinyl, $CF_3$, $CHF_2$ or $CH_2F$;

$R^2$ is H, OH, OMe or F;

$R^{2a}$ is H, Me or F;

$R^3$ is H, Me, Et, or $CF_3$;

A is

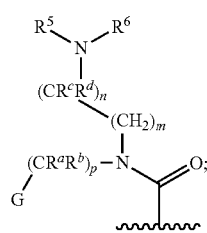

G is phenyl optionally substituted by one to four $R^e$ groups or a 5-6 membered heteroaryl optionally substituted by a halogen;

$R^5$ and $R^6$ are independently H, $OCH_3$, $C_3$-$C_6$-cycloalkyl optionally substituted with F, OH, $C_1$-$C_3$ alkyl or $O(C_1$-$C_3$ alkyl), 4-6 membered heterocycle optionally substituted with F, OH, $C_1$-$C_3$ alkyl, cyclopropylmethyl or $C(=O)(C_1$-$C_3$ alkyl), or $C_1$-$C_6$-alkyl optionally substituted with one or more groups independently selected from OH, oxo, $O(C_1$-$C_6$-alkyl), CN, F, $NH_2$, $NH(C_1$-$C_6$-alkyl), $N(C_1$-$C_6$-alkyl)$_2$, cyclopropyl, phenyl, imidazolyl, piperidinyl, pyrrolidinyl, morpholinyl, tetrahydrofuranyl, oxetanyl or tetrahydropyranyl, or $R^5$ and $R^6$ together with the nitrogen to which they are attached form a 4-7 membered heterocyclic ring optionally substituted with one or more groups independently selected from OH, halogen, oxo, $CF_3$, $CH_2CF_3$, $CH_2CH_2OH$, $O(C_1$-$C_3$ alkyl), $C(=O)CH_3$, $NH_2$, NHMe, $N(Me)_2$, $S(O)_2CH_3$, cyclopropylmethyl and $C_1$-$C_3$ alkyl, or $R^c$ is hydrogen and $R^d$ and $R^6$ together with the atoms to which they are attached form a 4 to 6 membered heterocyclic ring having one nitrogen atom;

$R^a$ and $R^b$ are H, or $R^a$ is H, and $R^b$ and $R^6$ together with the atoms to which they are attached form a 5-6 membered heterocyclic ring having one or two ring nitrogen atoms;

$R^c$ and $R^d$ are H or Me, or $R^c$ and $R^d$ together with the atom to which they are attached from a cyclopropyl ring;

each $R^e$ is independently halogen, $C_1$-$C_6$-alkyl, $C_3$-$C_6$-cycloalkyl, O—($C_1$-$C_6$-alkyl), $CF_3$, $OCF_3$, $S(C_1$-$C_6$-alkyl), CN, $OCH_2$-phenyl, $NH_2$, $NO_2$, NH—($C_1$-$C_6$-alkyl), N—($C_1$-$C_6$-alkyl)$_2$, piperidine, pyrrolidine, $CH_2F$, $CHF_2$, $OCH_2F$, $OCHF_2$, OH, $SO_2(C_1$-$C_6$-alkyl), $C(O)NH_2$, $C(O)NH(C_1$-$C_6$-alkyl), and $C(O)N(C_1$-$C_6$-alkyl)$_2$;

m and n are independently 0, 1, 2 or 3 with the proviso that (m+n) must equal 2, 3 or 4; and p is 0 or 1.

In general, the invention includes compounds of the Formula I:

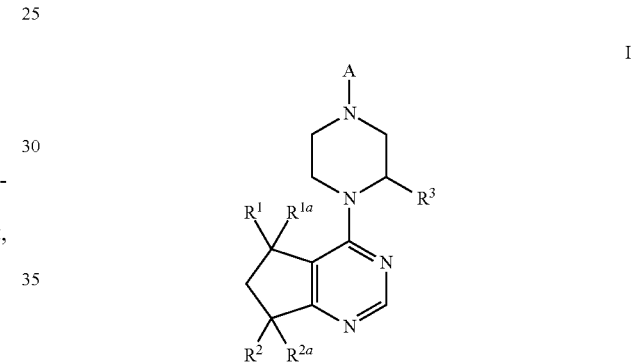

I and resolved enantiomers, resolved diastereomers, and pharmaceutically acceptable salts thereof, wherein:

$R^1$ and $R^{1a}$ are independently selected from H, Me, Et, vinyl, $CF_3$, $CHF_2$ or $CH_2F$;

$R^2$ is H, OH, OMe or F;

$R^{2a}$ is H, Me or F;

$R^3$ is H, Me, Et, or $CF_3$;

A is

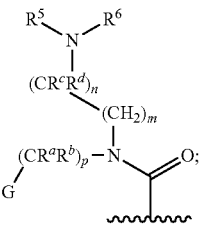

G is phenyl optionally substituted by one to four $R^e$ groups or a 5-6 membered heteroaryl optionally substituted by a halogen;

$R^5$ and $R^6$ are independently H, $OCH_3$, $C_3$-$C_6$-cycloalkyl optionally substituted with F, OH, $C_1$-$C_3$ alkyl or $O(C_1$-$C_3$ alkyl), 4-6 membered heterocycle optionally substituted with F, OH, $C_1$-$C_3$ alkyl, cyclopropylmethyl or $C(=O)(C_1$-$C_3$ alkyl), or $C_1$-$C_6$-alkyl optionally substituted with one or more groups independently selected from OH, oxo, O(C₁-C₆-alkyl), CN, F, NH₂, NH(C₁-C₆-alkyl), N(C₁-C₆-alkyl)₂, cyclopropyl, phenyl, imidazolyl, piperidinyl, pyrrolidinyl, morpholinyl, tetrahydrofuranyl, oxetanyl or tetrahydropyranyl, or R⁵ and R⁶ together with the nitrogen to which they are attached form a 4-7 membered heterocyclic ring optionally substituted with one or more groups independently selected from OH, halogen, oxo, CF₃, CH₂CF₃, CH₂CH₂OH, O(C₁-C₃ alkyl), C(=O)CH₃, NH₂, NHMe, N(Me)₂, S(O)₂CH₃, cyclopropylmethyl and C₁-C₃ alkyl;

Rᵃ and Rᵇ are H, or Rᵃ is H, and Rᵇ and R⁶ together with the atoms to which they are attached form a 5-6 membered heterocyclic ring having one or two ring nitrogen atoms;

Rᶜ and Rᵈ are H or Me, or Rᶜ and Rᵈ together with the atom to which they are attached from a cyclopropyl ring;

each Rᵉ is independently halogen, C₁-C₆-alkyl, C₃-C₆-cycloalkyl, O—(C₁-C₆-alkyl), CF₃, OCF₃, S(C₁-C₆-alkyl), CN, OCH₂-phenyl, NH₂, NO₂, NH—(C₁-C₆-alkyl), N—(C₁-C₆-alkyl)₂, piperidine, pyrrolidine, CH₂F, CHF₂, OCH₂F, OCHF₂, OH, SO₂(C₁-C₆-alkyl), C(O)NH₂, C(O)NH(C₁-C₆-alkyl), and C(O)N(C₁-C₆-alkyl)₂;

m and n are independently 0, 1 or 2, with the proviso that (m+n) must equal 2, 3 or 4; and p is 0 or 1.

Referring to the G group of Formula I, examples include phenyl ("Ph") optionally substituted with one or more Rᵉ groups independently selected from F, Cl, Br, I, methyl, ethyl, isopropyl, tert-butyl, cyclopropyl, CN, CF₃, OMe, OEt, OCF₃, NO₂, SMe and OCH₂Ph. Exemplary embodiments of G include phenyl, 2-chlorophenyl, 3-chlorophenyl, 4-chlorophenyl, 4-fluorophenyl, 4-bromophenyl, 4-methylphenyl, 4-ethylphenyl, 4-isopropylphenyl, 4-trifluoromethylphenyl, 4-cyanophenyl, 4-methoxyphenyl, 4-ethoxyphenyl, 4-thiomethylphenyl, 4-trifluoromethoxyphenyl, 4-cyclopropylphenyl, 4-chloro-3-fluorophenyl, 3,4-difluorophenyl, 4-bromo-3-fluorophenyl, 3-fluoro-4-methylphenyl, 3-fluoro-4-methoxyphenyl, 3-fluoro-4-trifluoromethylphenyl, 4-cyano-3-fluorophenyl, 3,4-dichlorophenyl, 2,4-dichlorophenyl, 2,4-difluorophenyl, 2-chloro-4-fluorophenyl, 2-fluoro-4-chlorophenyl, 3,5-dichlorophenyl. 3,5-difluorophenyl, 3-chloro-5-fluorophenyl, 3-chloro-4-fluorophenyl, 3-bromo-4-fluorophenyl, 3,5-difluoro-4-chlorophenyl, 2,3-difluoro-4-chlorophenyl, 2,5-difluoro-4-chlorophenyl, 3,5-difluoro-4-bromophenyl, 2,3-difluoro-4-bromophenyl, 2,5-difluoro-4-bromophenyl, 4-(OCH₂Ph)-phenyl, 4-chlorophenyl, 2,4-dichlorophenyl, 3,4-dichlorophenyl, 4-chloro-3-fluorophenyl, 3-chloro-4-fluorophenyl, 3-fluoro-4-bromophenyl, 4-fluorophenyl, 3,4-difluorophenyl, 2,4-difluorophenyl 4-bromophenyl, 4-chloro-2-fluorophenyl, 4-methoxyphenyl, 4-methylphenyl, 4-cyanophenyl, 4-trifluoromethylphenyl, 4-iodophenyl, 4-nitrophenyl, 4-tert-butylphenyl, 2-fluorophenyl, 3-trifluoromethylphenyl, 2-fluoro-4-trifluoromethylphenyl, 3-fluoro-4-trifluoromethoxyphenyl, 3-fluoro-4-trifluoromethylphenyl and 4-trifluoromethoxyphenyl.

Referring to the G group of Formula I, the phrase "5-6 membered heteroaryl optionally substituted by a halogen" includes thiophenes and pyridines, optionally substituted by halogens. Particular examples include, but are not limited to, the structures:

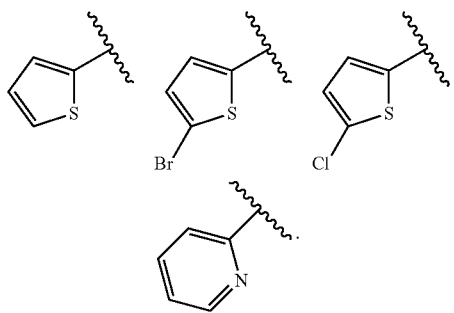

In one embodiment of Formula I, R³ is H.

In another embodiment of Formula I, R³ is methyl, wherein said methyl is optionally in the (S) configuration.

In another embodiment of Formula I, R³ is ethyl.

In one embodiment of Formula I, R¹ is methyl, wherein said methyl is optionally in the (R) configuration. In certain embodiments of Formula I, R¹ᵃ is H. In certain embodiments of Formula I, R¹ and R¹ᵃ are both methyl.

In another embodiment of Formula I, R¹ is H. In certain embodiments of Formula I, R¹ᵃ is H.

In another embodiment of Formula I, R¹ is ethyl. In certain embodiments of Formula I, R¹ᵃ is H.

In another embodiment of Formula I, R¹ is CH=CH₂ (vinyl). In certain embodiments of Formula I, R¹ᵃ is H.

In another embodiment of Formula I, R¹ is CH₂OH. In certain embodiments of Formula I, R¹ᵃ is H.

In one embodiment of Formula I, R¹ᵃ is H.

In one embodiment of Formula I, R² and R²ᵃ are H.

In another embodiment of Formula I, R² and R²ᵃ are F.

In another embodiment of Formula I, R² is F and R²ᵃ is H.

In another embodiment of Formula I, R² is OH. In certain embodiments of Formula I, R²ᵃ is H.

In another embodiment of Formula I, R² is OMe.

In one embodiment of Formula I, G is phenyl optionally substituted with one to four Rᵉ groups.

In one embodiment of Formula I, G is phenyl optionally substituted with one to four groups independently selected from F, Cl, Br, I, methyl, ethyl, isopropyl, tert-butyl, cyclopropyl, CN, CF₃, OMe, OEt, OCF₃, NO₂, SMe and OCH₂Ph. Exemplary embodiments of G include phenyl, 2-chlorophenyl, 3-chlorophenyl, 4-chlorophenyl, 4-fluorophenyl, 4-bromophenyl, 4-methylphenyl, 4-ethylphenyl, 4-isopropylphenyl, 4-trifluoromethylphenyl, 4-cyanophenyl, 4-methoxyphenyl, 4-ethoxyphenyl, 4-thiomethylphenyl, 4-trifluoromethoxyphenyl, 4-cyclopropylphenyl, 4-chloro-3-fluorophenyl, 3,4-difluorophenyl, 4-bromo-3-fluorophenyl, 3-fluoro-4-methylphenyl, 3-fluoro-4-methoxyphenyl, 3-fluoro-4-trifluoromethylphenyl, 4-cyano-3-fluorophenyl, 3,4-dichlorophenyl, 2,4-dichlorophenyl, 2,4-difluorophenyl, 2-chloro-4-fluorophenyl, 2-fluoro-4-chlorophenyl, 3,5-dichlorophenyl. 3,5-difluorophenyl, 3-chloro-5-fluorophenyl, 3-chloro-4-fluorophenyl, 3-bromo-4-fluorophenyl, 3,5-difluoro-4-chlorophenyl, 2,3-difluoro-4-chlorophenyl, 2,5-difluoro-4-chlorophenyl, 3,5-difluoro-4-bromophenyl, 2,3-difluoro-4-bromophenyl, 2,5-difluoro-4-bromophenyl, 4-(OCH₂Ph)-phenyl, 4-chlorophenyl, 2,4-dichlorophenyl, 3,4-dichlorophenyl, 4-chloro-3-fluorophenyl, 3-chloro-4-fluorophenyl, 3-fluoro-4-bromophenyl, 4-fluorophenyl, 3,4-difluorophenyl, 2,4-difluorophenyl 4-bromophenyl, 4-chloro-2-fluorophenyl, 4-methoxyphenyl, 4-methylphenyl, 4-cyanophenyl, 4-trifluoromethylphenyl, 4-iodophenyl, 4-nitrophenyl, 4-tert-butylphenyl, 2-fluorophenyl, 3-trifluoromethylphenyl, 2-fluoro-4-trifluoromethylphenyl, 3-fluoro-4-trifluoromethoxyphenyl, 3-fluoro-4-trifluoromethylphenyl and 4-trifluoromethoxyphenyl.

In one embodiment of Formula I, G is 4-chlorophenyl, 4-fluorophenyl, 4-bromophenyl, 4-iodophenyl, 4-trifluoromethylphenyl, 4-trifluormethoxyphenyl, 4-thiomethylphenyl, 3-fluoro-4-chlorophenyl, 2,4-dichlorophenyl or 3,4-dichlorophenyl.

In one embodiment of Formula I, G may be a 5-6 membered monocyclic heteroaryl optionally substituted by one or more halogens. In certain embodiments, G may be a thiophene or a pyridine, optionally substituted by one or more halogens. In certain embodiments, G is substituted by one halogen. Particular embodiments include:

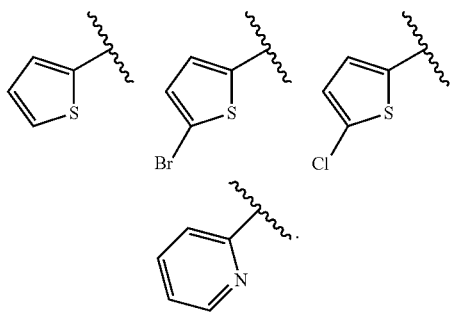

In one embodiment of Formula I, $R^5$ is H or ethyl.
In one embodiment of Formula I, $R^6$ is H or ethyl.
In one embodiment of Formula I, $R^6$ is hydrogen, ethyl or isopropyl.
In one embodiment of Formula I, $R^a$ and $R^b$ are H.
In one embodiment of Formula I, $R^c$ and $R^d$ are H.
In one embodiment, $R^c$ is hydrogen and $R^d$ and $R^6$ together with the atoms to which they are attached form a 4 to 6 membered heterocyclic ring having one nitrogen atom. In certain embodiments, m is 0, $R^c$ is hydrogen, and $R^d$ and $R^6$ together with the atoms to which they are attached form a 4 to 6 membered heterocyclic ring having one nitrogen atom, such that A has the formula:

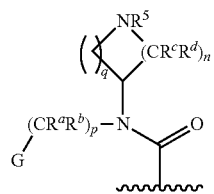

wherein q is 1 or 2 and n is 1 or 2. In certain embodiments, n is 1 and q is 1, n is 1 and q is 2, or
n is 2 and q is 2.

In one embodiment of Formula I, m and n are independently 0, 1 or 2, with the proviso that (m+n) must equal 2, 3 or 4. In particular embodiments, m is 0 and n is 2, m is 1 and n is 2, m is 2 and n is 2, m is 1 and n is 1, m is 2 and n is 1, or m is 2 and n is 0.

In one embodiment of Formula I, m and n are both 1.

In another embodiment of Formula I, m is 2 and n is 0. In another embodiment of Formula I, n is 2 and m is 0.

In one embodiment of Formula I, m is 1, n is 1, p is 0, such that A is represented by the Formula 1:

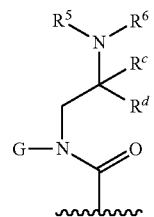

wherein G, $R^5$, $R^6$, $R^c$ and $R^d$ are as defined herein.
In certain embodiments of Formula 1, $R^c$ and $R^d$ are H.
In certain embodiment of Formula 1, $R^5$ is H or ethyl.
In certain embodiment of Formula 1, $R^6$ is H or ethyl.
In certain embodiments of Formula I, m is 1, n is 1 and p is 1, such that A is represented by the Formula 2:

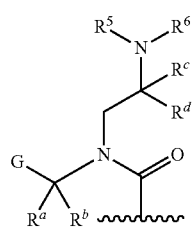

wherein G, $R^6$, $R^7$, and $R^8$ are as defined herein.
In certain embodiments of Formula 2, $R^a$ and $R^b$ are H.
In certain embodiments of Formula 2, $R^c$ and $R^d$ are H.
In certain embodiment of Formula 2, $R^5$ is H or ethyl.
In certain embodiment of Formula 2, $R^6$ is H or ethyl.
In particular embodiments, A is:

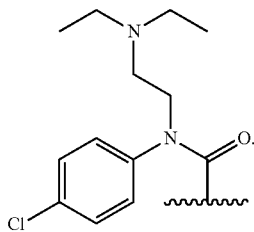 [SMILES: *C(=O)N(CCN(CC)CC)c1ccc(Cl)cc1]

In additional embodiments, A is selected from the structures:

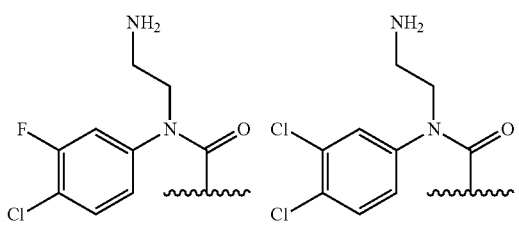

-continued
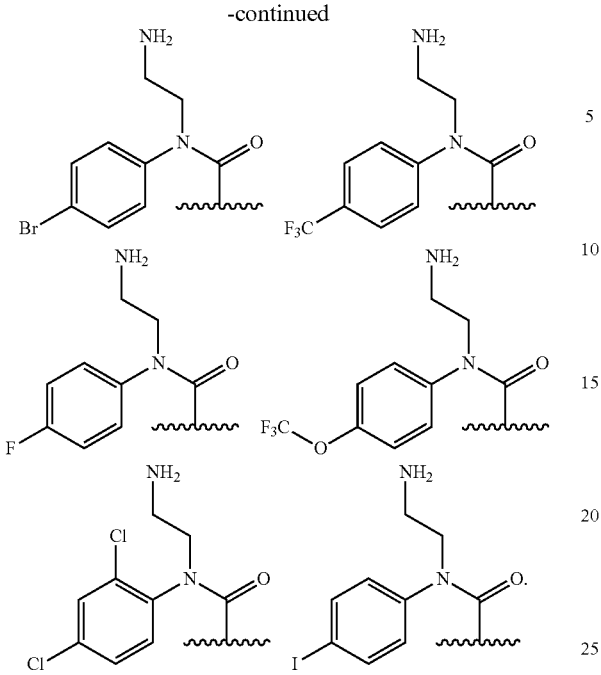
In additional embodiments, A is:
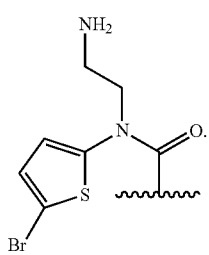 [SMILES: *C(=O)N(CCN)c1ccc(Br)s1]
In particular embodiments, A is selected from:
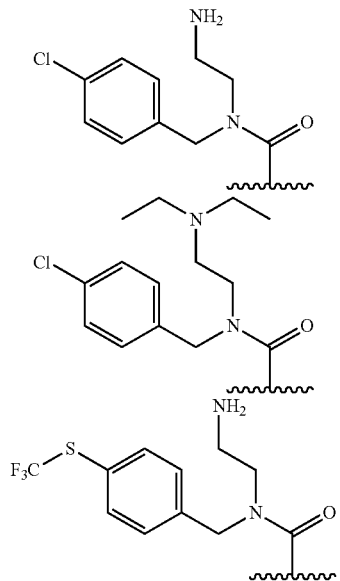
-continued
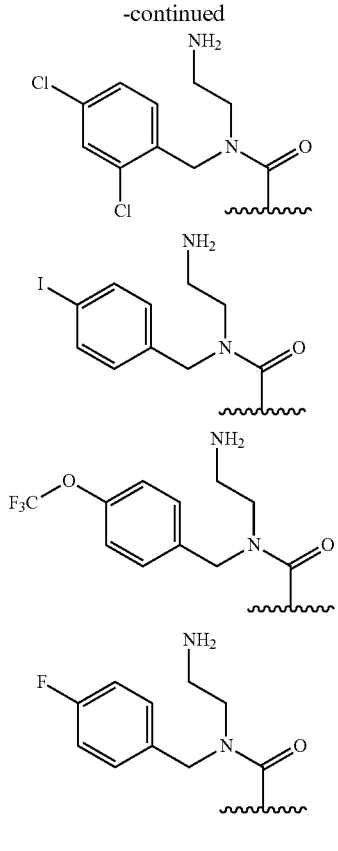
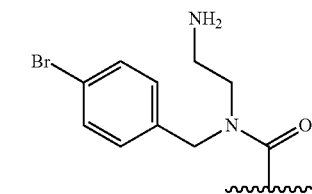
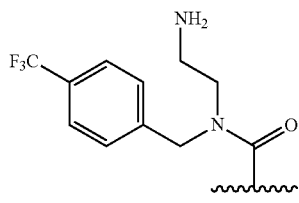
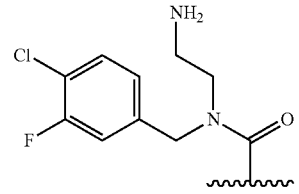
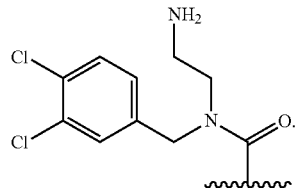

In particular embodiments, A is:

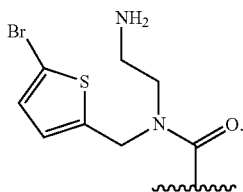

In certain embodiments, the salt is a "pharmaceutically acceptable salt" which, unless otherwise indicated, includes salts that retain the biological effectiveness of the corresponding free acid or base of the specified compound and are not biologically or otherwise undesirable.

The compounds of Formula I also include other salts of such compounds which are not necessarily pharmaceutically acceptable salts, and which may be useful as intermediates for preparing and/or purifying compounds of Formula I and/or for separating enantiomers of compounds of Formula I.

Synthesis of Compounds of Formula I

Compounds of the present invention may be synthesized by synthetic routes that include processes analogous to those well-known in the chemical arts, particularly in light of the description contained herein. The starting materials are generally available from commercial sources such as Sigma-Aldrich (St. Louis, Mo.), Alfa Aesar (Ward Hill, Mass.), or TCI (Portland, Oreg.), or are readily prepared using methods well known to those skilled in the art (e.g., prepared by methods generally described in Louis F. Fieser and Mary Fieser, *Reagents for Organic Synthesis*, v. 1-19, Wiley, N.Y. (1967-1999 ed.), or *Beilsteins Handbuch der organischen Chemie*, 4, Aufl. ed. Springer-Verlag, Berlin, including supplements (also available via the Beilstein online database).

For illustrative purposes, Schemes 1 to 8 show general methods for preparing the compounds of the present invention, as well as key intermediates. For a more detailed description of the individual reaction steps, see the Examples section below. Those skilled in the art will appreciate that other synthetic routes may be used to synthesize the inventive compounds. Although specific starting materials and reagents are depicted in the Schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

Scheme 1

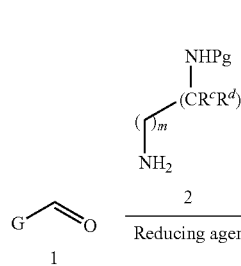

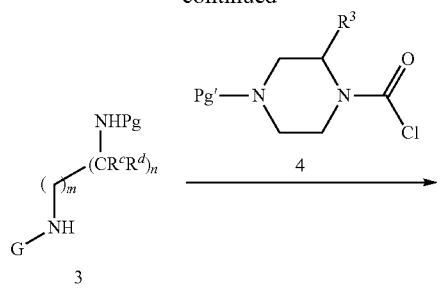

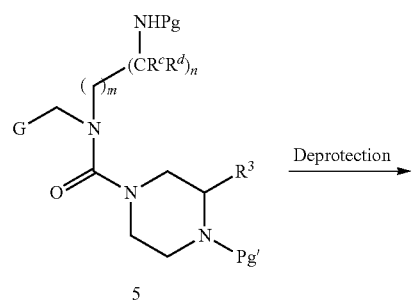

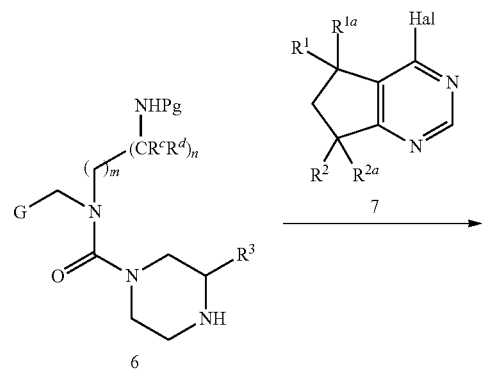

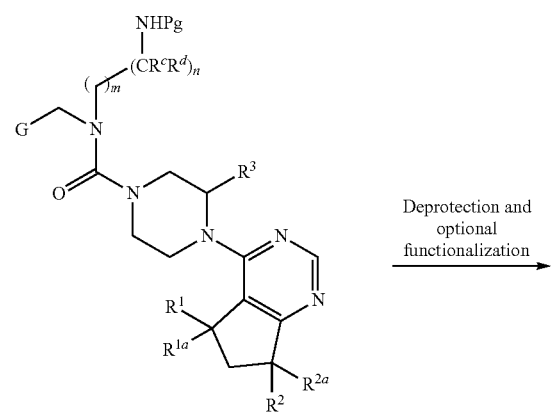

-continued

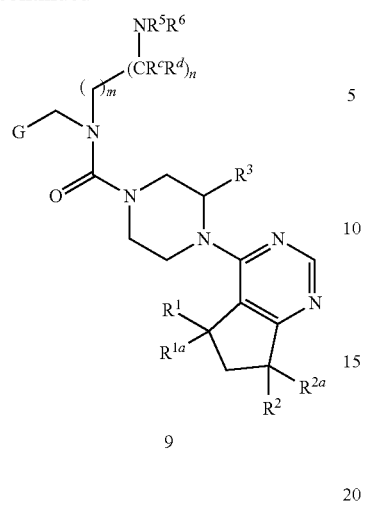

9

Scheme 1 shows a method of preparing compound 9 of Formula I, wherein p is 1; $R^a$ and $R^b$ are H; $R^2$, $R^{2a}$, $R^1$, $R^{1a}$, $R^3$, $R^5$, $R^6$, $R^c$, $R^d$, m and n are defined herein; and Pg and Pg' are amine protecting groups with mutually exclusive removal conditions (e.g. Pg=Boc and Pg'=Cbz—see, for example, 'Protective Groups in Organic Synthesis' by Greene and Wuts, Wiley-Interscience, third edition, Chapter 7). Reductive amination of the amine 2 onto the aldehyde 1 using standard conditions, such as NaBH(OAc$_3$)/AcOH at 0° C. to 50° C. gives the substituted amine 3. Acylation of this substituted amine 3 with the substituted acylpiperazine 4 in the presence of a base (such as Hunig's base) at −20° C. to 100° C. gives the protected piperazine 5. Removal of this protecting group (e.g. for a Cbz group, hydrogenolysis, etc.) gives the piperazine 6. Treatment of this piperazine 6 with the halogenated pyrimidine 7 at 25° C. to 250° C. and/or at high pressure and/or microwave assistance gives the intermediate 8. Deprotection of the amine, (for example, for a Boc group, using HCl in dioxane at 0° C. to 50° C.) and final optional functionalization of the amine (e.g. alkylation, reductive amination or acylation under standard conditions to introduce new substituents) gives rise to the final compounds 9. If need be, these analogues may then be subject to separation techniques to give the single enantiomers.

Scheme 2

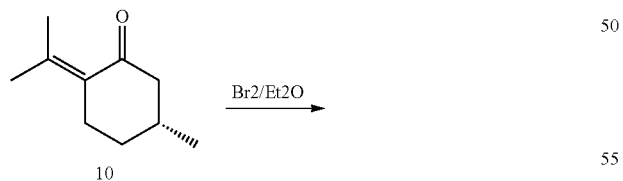

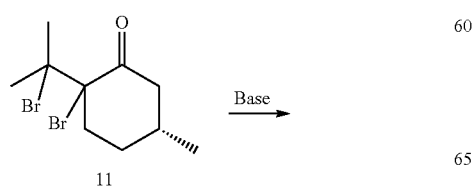

-continued

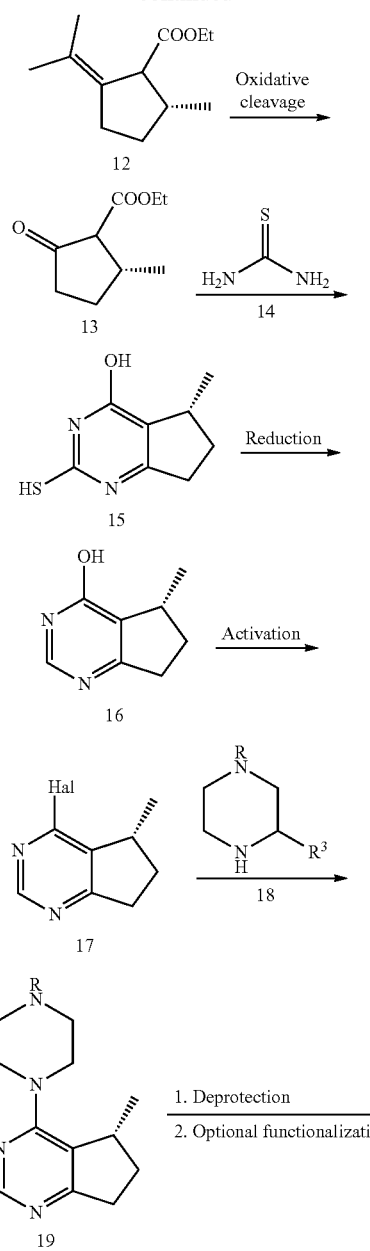

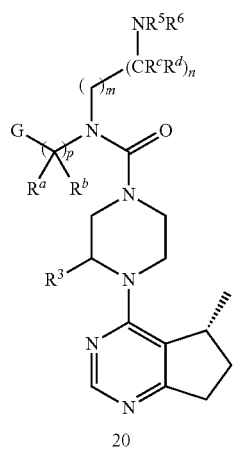

19
-continued

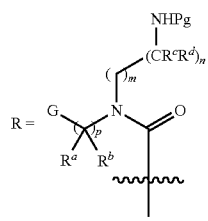

20
-continued

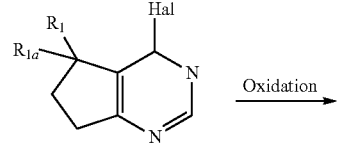

Scheme 2 shows a method of preparing compound 20 of Formula I, wherein $R^1$, $R^2$ and $R^{2a}$ are hydrogen; $R^{1a}$ is Me; and $R^3$, $R^5$, $R^6$, $R^a$, $R^b$, $R^c$, $R^d$, m, n and p are as defined herein. According to Scheme 2, bromination of (+)-pulegone 10 with bromine gives the dibromide 11. The treatment of the dibromide 11 with a base, such as sodium ethoxide, provides the pulegenate 12. Oxidative cleavage of the pulegenate 12 using, for example, ozonolysis at low temperature followed by reductive workup (e.g. Zn) or NaIO$_4$/OsO$_4$ at 5° C. to 50° C.) gives the keto ester 13. Treatment of the keto ester 13 with thiourea in the presence of a base, such as KOH in ethanol, followed by reduction of the mercapto group under standard conditions (e.g. Raney Ni catalyst in ammonia) affords the hydroxypyrimidine 16. Activation of compound 16 (e.g. halogenation) using, for example, POCl$_3$ or SOCl$_2$ at −20° C. to 100° C. to give the chloropyrimidine, gives the functionalized pyrimidine-cyclopentane unit 17. Displacement of the leaving group, using a suitable protected/substituted piperidine 18 at 0° C. to 150° C. gives the piperidine 19. Deprotection of the amine, (for example, for a Boc group, using HCl in dioxane at 0° C. to 50° C.) and final optional functionalization of the amine (e.g. alkylation, reductive amination or acylation to introduce new substituents) gives rise to the final compound 20. If need be, these analogues may then be subject to separation techniques to give the single enantiomers.

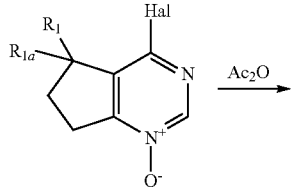

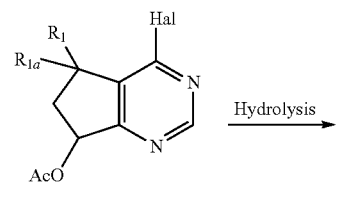

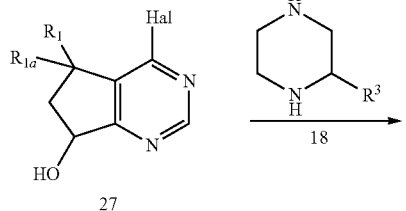

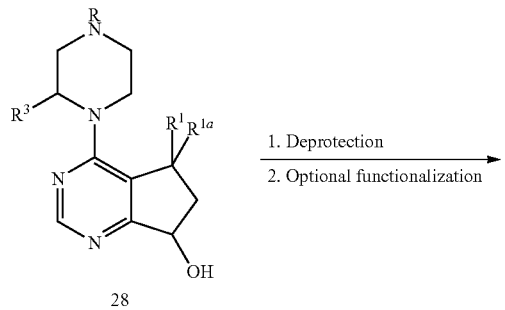

Scheme 3

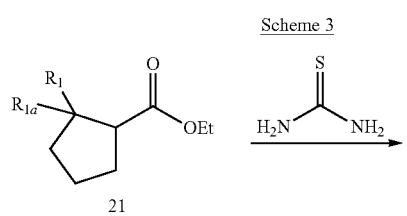

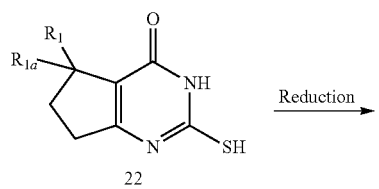

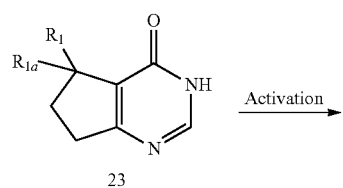

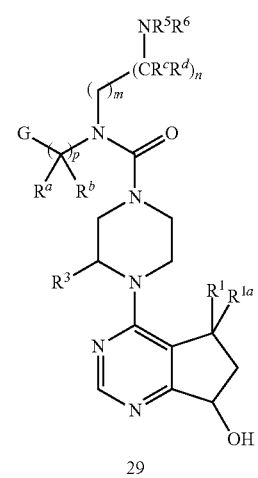

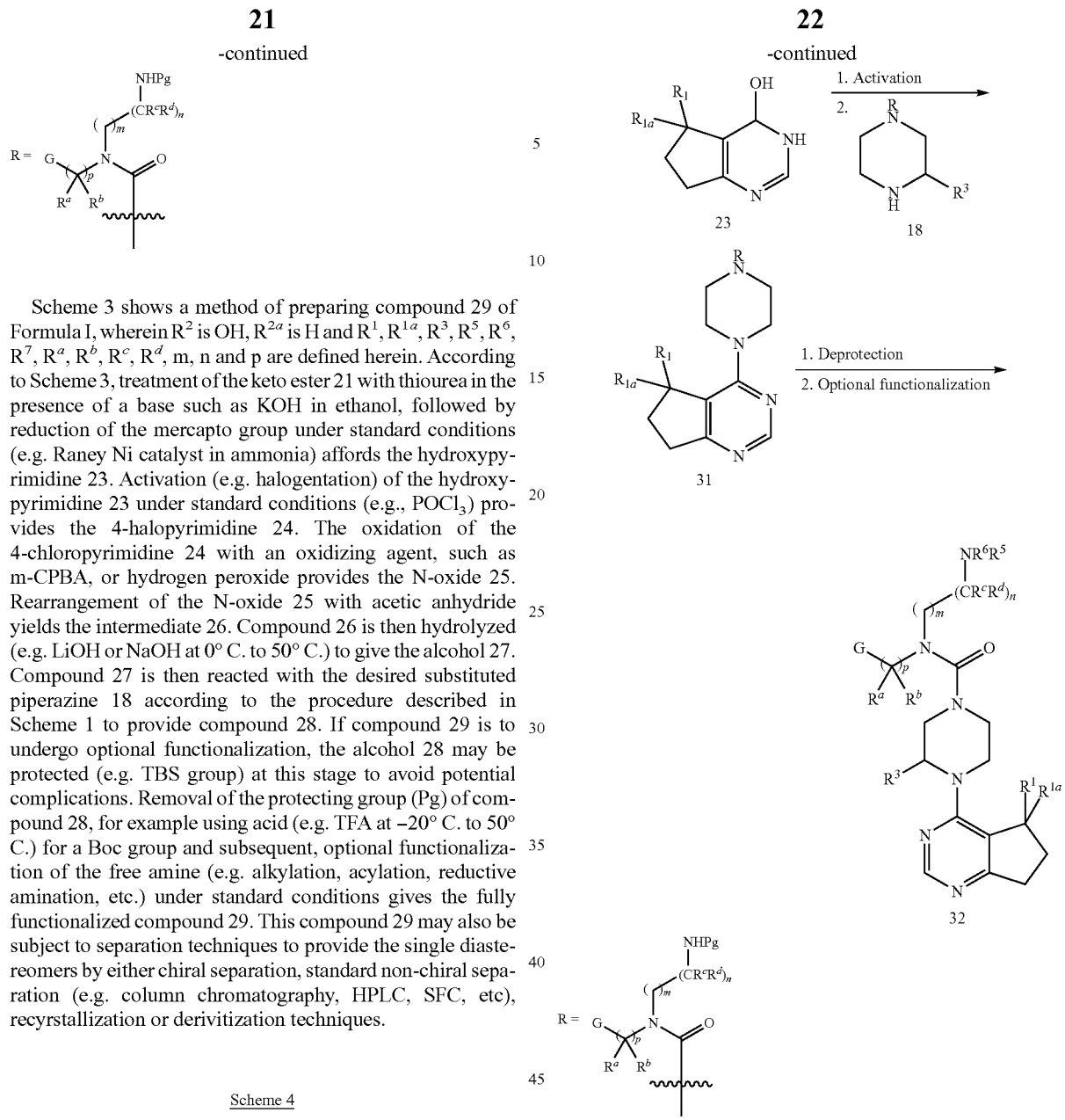

Scheme 3 shows a method of preparing compound 29 of Formula I, wherein $R^2$ is OH, $R^{2a}$ is H and $R^1$, $R^{1a}$, $R^3$, $R^5$, $R^6$, $R^7$, $R^a$, $R^b$, $R^c$, $R^d$, m, n and p are defined herein. According to Scheme 3, treatment of the keto ester 21 with thiourea in the presence of a base such as KOH in ethanol, followed by reduction of the mercapto group under standard conditions (e.g. Raney Ni catalyst in ammonia) affords the hydroxypyrimidine 23. Activation (e.g. halogentation) of the hydroxypyrimidine 23 under standard conditions (e.g., $POCl_3$) provides the 4-halopyrimidine 24. The oxidation of the 4-chloropyrimidine 24 with an oxidizing agent, such as m-CPBA, or hydrogen peroxide provides the N-oxide 25. Rearrangement of the N-oxide 25 with acetic anhydride yields the intermediate 26. Compound 26 is then hydrolyzed (e.g. LiOH or NaOH at 0° C. to 50° C.) to give the alcohol 27. Compound 27 is then reacted with the desired substituted piperazine 18 according to the procedure described in Scheme 1 to provide compound 28. If compound 29 is to undergo optional functionalization, the alcohol 28 may be protected (e.g. TBS group) at this stage to avoid potential complications. Removal of the protecting group (Pg) of compound 28, for example using acid (e.g. TFA at −20° C. to 50° C.) for a Boc group and subsequent, optional functionalization of the free amine (e.g. alkylation, acylation, reductive amination, etc.) under standard conditions gives the fully functionalized compound 29. This compound 29 may also be subject to separation techniques to provide the single diastereomers by either chiral separation, standard non-chiral separation (e.g. column chromatography, HPLC, SFC, etc), recyrstallization or derivitization techniques.

Scheme 4

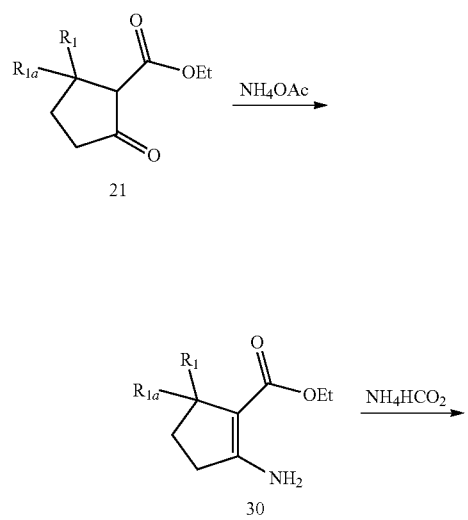

Scheme 4 shows an alternative method of preparing compound 32 of Formula I, wherein $R^2$ and $R^{2a}$ are H and $R^1$, $R^{1a}$, $R^3$, $R^5$, $R^6$, $R^7$, $R^a$, $R^b$, $R^c$, $R^d$, m, n and p are defined herein. According to Scheme 3, amination of keto ester 21 using an ammonia synthon gives compound 30. Pyrimidine formation using, for example, ammonium formate, in the presence of formamide at 50° C. to 250° C. and/or at high pressure and/or microwave assistance gives the bicyclic unit 23. Activation of compound 23 using, for example, $POCl_3$ or $SOCl_2$, gives the activated pyrimidine and displacement of this leaving group, using a suitable protected/substituted piperidine 18 at 0° C. to 150° C. gives the piperidine 31. Deprotection of the amine, (for example, for a Boc group, using HCl in dioxane at 0° C. to 50° C.) and final optional functionalization of the amine (e.g. alkylation, reductive amination or acylation to introduce new substituents) gives rise to the final compounds 32. If need be, these analogues may then be subject to separation techniques to give the single enantiomers.

Scheme 5

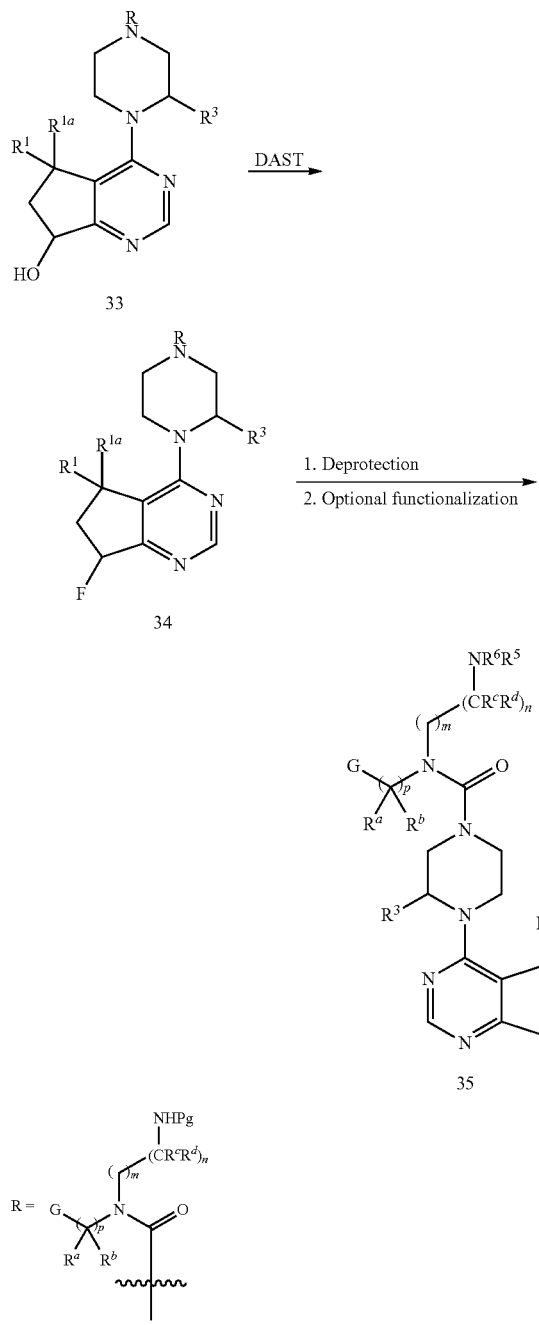

Scheme 6

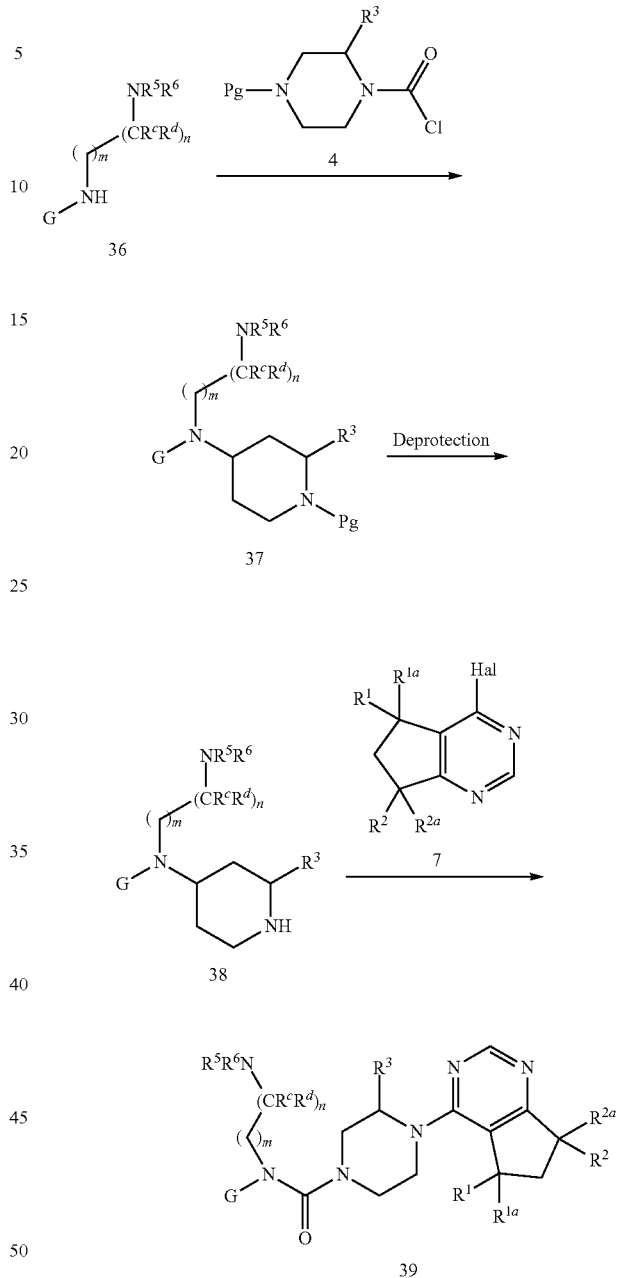

Scheme 5 shows a method of preparing compound 35 of Formula I, wherein $R^2$ is fluorine, $R^{2a}$ is hydrogen and $R^1$, $R^{1a}$, $R^3$, $R^5$, $R^6$, $R^7$, $R^a$, $R^b$, $R^c$, $R^d$, m, n and p are defined herein. According to Scheme 5, treatment of the alcohol 33 with a fluorinating agent, such as DAST at −78° C. to 100° C., gives the fluoro derivative 34. Deprotection of the amine, (for example, for a Boc group, using HCl in dioxane at 0° C. to 50° C.) and final optional functionalization of the amine (e.g. alkylation, reductive amination or acylation to introduce new substituents) gives rise to the final compound 35. If need be, these analogues may then be subject to separation techniques to give the single enantiomers.

Scheme 6 shows a method of preparing compound 39 of Formula I, wherein p is 0; $NR^5R^6$ is such that the amine cannot be further acylated by compound 4; and $R^2$, $R^{2a}$, $R^1$, $R^{1a}$, $R^3$, $R^5$, $R^6$, $R^7$, $R^a$, $R^b$, $R^c$, $R^d$, m and n are defined herein. Acylation of the substituted amine 36 with the substituted acylpiperazine 4 in the presence of a base (such as Hunig's base) at −20° C. to 100° C. gives the protected piperazine 37 (Pg=protecting group). Removal of this protecting group (e.g. for a Boc group, HCl in dioxane, or for a Cbz group, hydrogenation, etc.) gives the piperazine 38. Treatment of this piperazine 38 with the halogenated pyrimidine 7 at 50° C. to 250° C. and/or at high pressure and/or microwave assistance gives the product 39. If need be, these analogues may then be subject to separation techniques to give the single enantiomers.

Scheme 7

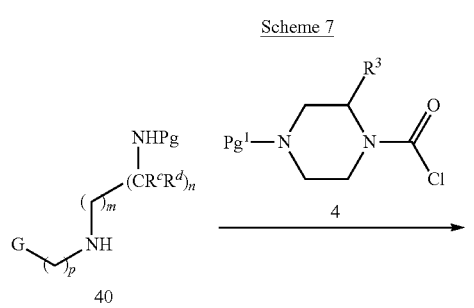
40

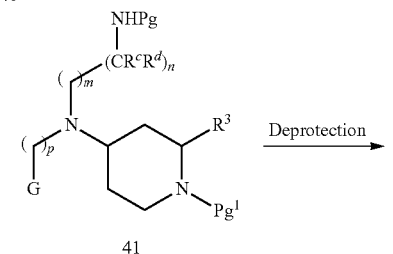
41

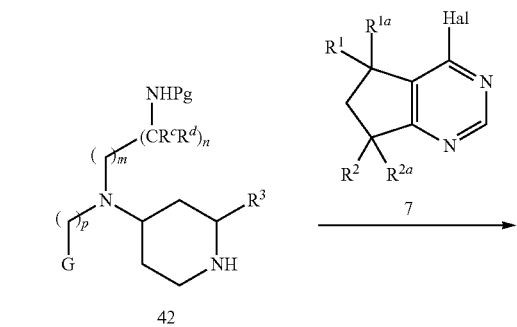
42

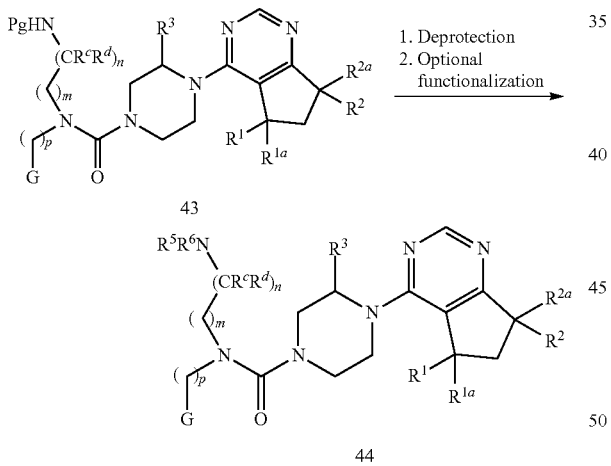
43

44

Scheme 8

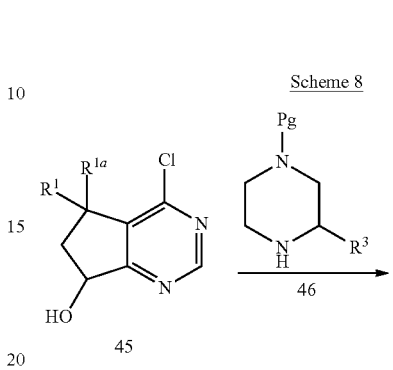
45

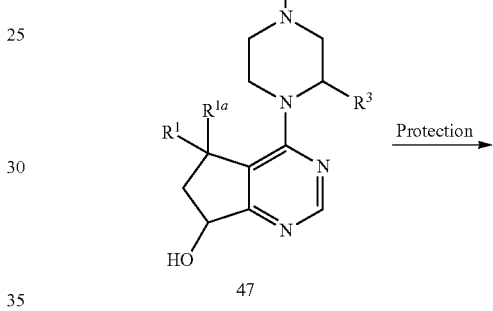
47

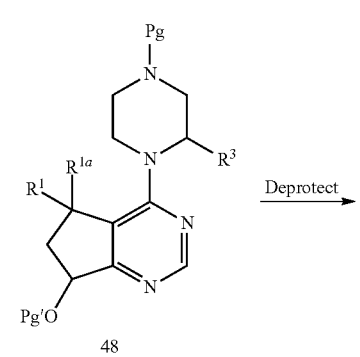
48

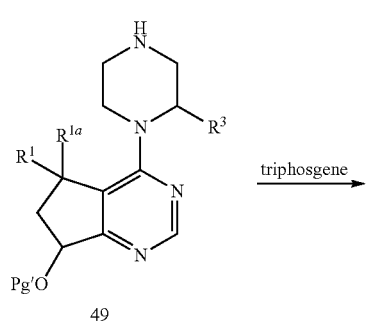
49

Scheme 7 demonstrates an alternative way for the formation of (44) of Formula I, wherein $R^2$, $R^{2a}$, $R^1$, $R^{1a}$, $R^3$, $R^5$, $R^6$, $R^7$, Ra, Rb, Rc, Rd, m, p and n are defined herein and Pg and $Pg^1$ are protecting groups with mutually exclusive removal conditions (e.g. Boc and Cbz groups). Acylation of the substituted amine 40 with the substituted acylpiperazine 4 in the presence of a base (such as Hunig's base) at −20° C. to 100° C. gives the protected piperazine 41 (Pg=protecting group). Removal of this protecting group (e.g. for a Boc group, HCl in dioxane, or for a Cbz group, hydrogenation, etc.) gives the piperazine 42. Treatment of this piperazine 42 with the halogenated pyrimidine 7 at 50° C. to 250° C. and/or at high pressure and/or microwave assistance gives the intermediate 43. Removal of the amine protecting group (e.g. for a Boc, HCl in dioxane, at 0° C. to 50° C., etc.) and subsequent optional functionalization (e.g. alkylation, reductive amination or acylation to introduce new substituents) gives rise to the final compound 44. If need be, these analogues may then be subject to separation techniques to give the single enantiomers.

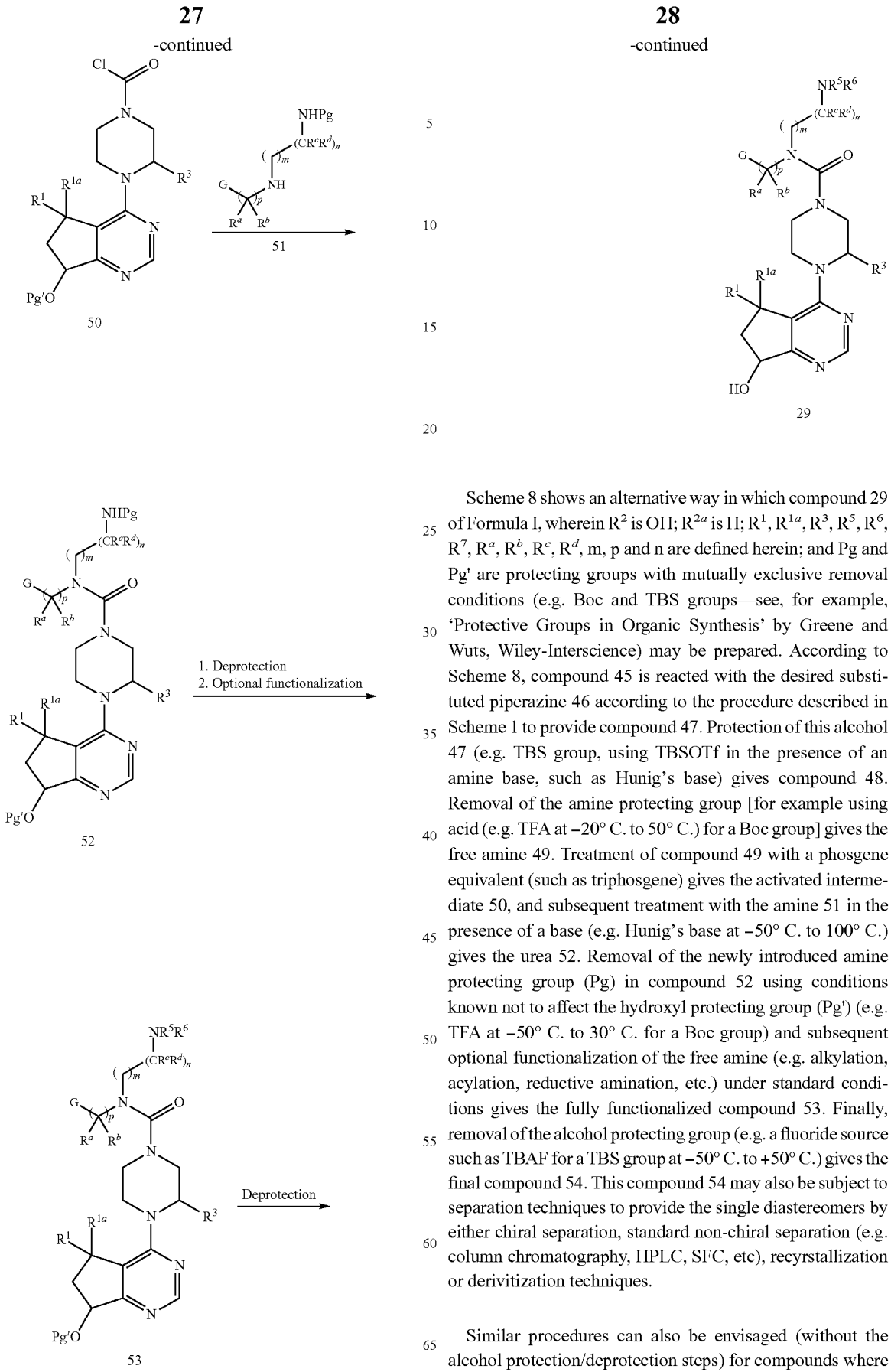

Scheme 8 shows an alternative way in which compound 29 of Formula I, wherein $R^2$ is OH; $R^{2a}$ is H; $R^1$, $R^{1a}$, $R^3$, $R^5$, $R^6$, $R^7$, $R^a$, $R^b$, $R^c$, $R^d$, m, p and n are defined herein; and Pg and Pg' are protecting groups with mutually exclusive removal conditions (e.g. Boc and TBS groups—see, for example, 'Protective Groups in Organic Synthesis' by Greene and Wuts, Wiley-Interscience) may be prepared. According to Scheme 8, compound 45 is reacted with the desired substituted piperazine 46 according to the procedure described in Scheme 1 to provide compound 47. Protection of this alcohol 47 (e.g. TBS group, using TBSOTf in the presence of an amine base, such as Hunig's base) gives compound 48. Removal of the amine protecting group [for example using acid (e.g. TFA at −20° C. to 50° C.) for a Boc group] gives the free amine 49. Treatment of compound 49 with a phosgene equivalent (such as triphosgene) gives the activated intermediate 50, and subsequent treatment with the amine 51 in the presence of a base (e.g. Hunig's base at −50° C. to 100° C.) gives the urea 52. Removal of the newly introduced amine protecting group (Pg) in compound 52 using conditions known not to affect the hydroxyl protecting group (Pg') (e.g. TFA at −50° C. to 30° C. for a Boc group) and subsequent optional functionalization of the free amine (e.g. alkylation, acylation, reductive amination, etc.) under standard conditions gives the fully functionalized compound 53. Finally, removal of the alcohol protecting group (e.g. a fluoride source such as TBAF for a TBS group at −50° C. to +50° C.) gives the final compound 54. This compound 54 may also be subject to separation techniques to provide the single diastereomers by either chiral separation, standard non-chiral separation (e.g. column chromatography, HPLC, SFC, etc), recyrstallization or derivitization techniques.

Similar procedures can also be envisaged (without the alcohol protection/deprotection steps) for compounds where $R^2$ is H or F instead of OH.

Accordingly, another aspect of the invention provides a method of preparing compounds of Formula I, comprising:

(a) reacting a compound having the formula:

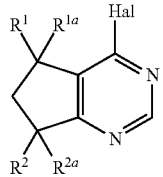

wherein $R^1$, $R^{1a}$, $R^2$ and $R^{2a}$ are as defined herein and Hal is a halogen, with a compound of the formula:

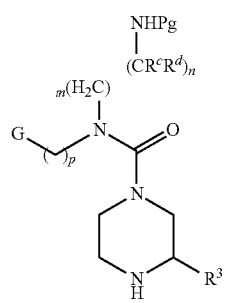

wherein G, $R^3$, $R^c$, $R^d$, n, m and p are as defined herein and Pg is a protecting group as defined herein, followed by deprotection and optional functionalization to prepare a compound of Formula I;

(b) activation of a compound of formula:

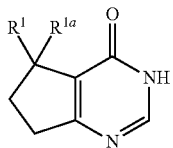

wherein $R^1$ and $R^{1a}$ are as defined herein, with $POCl_3$ or $SOCl_2$, followed by displacement with a compound of formula:

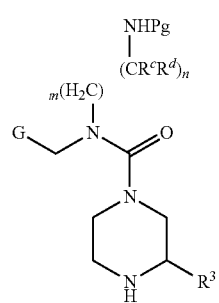

wherein G, $R^3$, $R^c$, $R^d$, n and m are as defined herein and Pg is a protecting group as defined herein, followed by deprotection and optional functionalization to prepare a compound of Formula I; or (c) reacting a compound of formula:

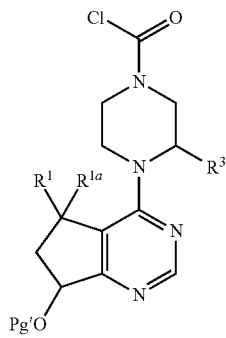

wherein $R^1$, $R^{1a}$ and $R^3$ are as defined herein and Pg' is a protective group as defined herein, with a compound of formula:

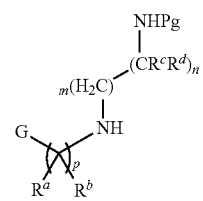

wherein G, $R^a$, $R^b$, $R^c$, $R^d$, n, m and p are as defined herein and Pg is a protecting group as defined herein, followed by deprotection and optional functionalization to prepare a compound of Formula I.

In preparing compounds of Formula I, protection of remote functionalities (e.g., primary or secondary amines, etc.) of intermediates may be necessary. The need for such protection will vary depending on the nature of the remote functionality and the conditions of the preparation methods. Suitable amino-protecting groups (NH-Pg) include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

Methods of Separation

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and diastereomers, and mixtures, racemic or otherwise, thereof. Accordingly, this invention also includes all such isomers, including diastereomeric mixtures, pure diastereomers and pure enantiomers of the compounds of this invention. Diastereomers have different physical properties, e.g., melting points, boiling points, spectral properties, and reactivities.

It may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography. One skilled in the art will apply techniques most likely to achieve the desired separation.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Enantiomers can also be separated by use of a chiral HPLC column.

A single stereoisomer, e.g., an enantiomer, substantially free of its stereoisomer may be obtained by resolution of the racemic mixture using a method such as formation of diastereomers using optically active resolving agents (Eliel, E. and Wilen, S. "Stereochemistry of Organic Compounds," John Wiley & Sons, Inc., New York, 1994; Lochmuller, C. H., (1975) *J. Chromatogr.*, 113(3):283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: "Drug Stereochemistry, Analytical Methods and Pharmacology," Irving W. Wainer, Ed., Marcel Dekker, Inc., New York (1993).

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. and Wilen, S. "Stereochemistry of Organic Compounds", John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob III. *J. Org. Chem.*, (1982) 47:4165), of the racemic mixture, and analyzing the $^1$H NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111).

By method (3), a racemic mixture of two enantiomers can be separated by chromatography using a chiral stationary phase ("Chiral Liquid Chromatography" (1989) W. J. Lough, Ed., Chapman and Hall, New York; Okamoto, *J. of Chromatogr.*, (1990) 513:375-378). Enriched or purified enantiomers can be distinguished by methods used to distinguish other chiral molecules with asymmetric carbon atoms, such as optical rotation and circular dichroism.

The compounds of the present invention may also exist in different tautomeric forms, and all such forms are embraced within the scope of the invention. For example, proton tautomers (also known as prototropic tautomers) include interconversions via migration of a proton, such as keto-enol and imine-enamine isomerizations. Valence tautomers include interconversions by reorganization of some of the bonding electrons.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

Administration and Pharmaceutical Formulations

The compounds of the invention may be administered by any convenient route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal.

The compounds may be administered in any convenient administrative form, e.g. tablets, powders, capsules, solutions, dispersions, suspensions, syrups, sprays, suppositories, gels, emulsions, patches, etc. Such compositions may contain components conventional in pharmaceutical preparations, e.g. diluents, carriers, pH modifiers, sweeteners, bulking agents, and further active agents. If parenteral administration is desired, the compositions will be sterile and in a solution or suspension form suitable for injection or infusion.

A typical formulation is prepared by mixing a compound of the present invention and a carrier or excipient. Suitable carriers and excipients are well known to those skilled in the art and are described in detail in, e.g., Howard C. Ansel et al., Pharmaceutical Dosage Forms and Drug Delivery Systems, (8$^{th}$ Ed. 2004); Alfonso R. Gennaro et al., Remington: The Science and Practice of Pharmacy, (20$^{th}$ Ed. 2000); and Raymond C. Rowe, Handbook of Pharmaceutical Excipients, (5$^{th}$ Ed. 2005). The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

One embodiment of the present invention includes a pharmaceutical composition comprising a compound of Formula I, or a stereoisomer or pharmaceutically acceptable salt thereof. In a further embodiment, the present invention provides a pharmaceutical composition comprising a compound of Formula I, or a stereoisomer or pharmaceutically acceptable salt thereof, together with a pharmaceutically acceptable carrier or excipient.

Methods of Treatment with Compounds of Formula I

The compounds of the present invention can be used as prophylactics or therapeutic agents for treating diseases or disorders mediated by modulation or regulation of AKT protein kinases, tyrosine kinases, additional serine/threonine kinases, and/or dual specificity kinases. AKT protein kinase mediated conditions that can be treated according to the methods of this invention include, but are not limited to, inflammatory, hyperproliferative cardiovascular, neurodegenerative, gynecological, and dermatological diseases and disorders.

In one embodiment, said pharmaceutical composition is for the treatment of hyperproliferative disorders, including cancers of the following categories: (1) Cardiac: sarcoma (angiosarcoma, fibrosarcoma, rhabdomyosarcoma, liposarcoma), myxoma, rhabdomyoma, fibroma, lipoma and teratoma; (2) Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma, non-small cell lung, small cell lung; (3) Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); (4) Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); (5) Liver: hepatoma (hepatocellular carcinoma), cholangiocarcinoma, hepatoblastoma, angiosarcoma, hepatocellular adenoma, hemangioma; (6) Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; (7) Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform. oligodendroglioma, schwannoma, retinoblastoma, congenital tumors), spinal cord neurofibroma, meningioma, glioma, sarcoma); (8) Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); (9) Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; (10) Skin: advanced melanoma, malignant melanoma, basal cell carcinoma, squamous cell carcinoma, Karposi's sarcoma, moles dysplastic nevi, lipoma, angioma, dermatofibroma, keloids, psoriasis; (11) Adrenal glands: neuroblastoma; (12) Breast: metastatic breast; breast adenocarcinoma; (13) Colon; (14) Oral cavity; (15) Hairy cell leukemia; (16) Head and neck; (17) and others including refractory metastatic disease; Kaposi's sarcoma; Bannayan-Zonana syndrome; and Cowden disease or Lhermitte-Duclos disease, among other kinds of hyperproliferative disorders.

Compounds and methods of this invention can be also used to treat diseases and conditions such as rheumatoid arthritis, osteoarthritis, Chron's disease, angiofibroma, ocular diseases (e.g., retinal vascularisation, diabetic retinopathy, age-related macular degeneration, macular degeneration, etc.), multiple sclerosis, obesity, restenosis, autoimmune diseases, allergy, asthma, endometriosis, atherosclerosis, vein graft stenosis, peri-anastomatic prothetic graft stenosis, prostate hyperplasia, chronic obstructive pulmonary disease, psoriasis, inhibition of neurological damage due to tissue repair, scar tissue formation (and can aid in wound healing), multiple sclerosis, inflammatory bowel disease, infections, particularly bacterial, viral, retroviral or parasitic infections (by increasing apoptosis), pulmonary disease, neoplasm, Parkinson's disease, transplant rejection (as an immunosupressant), septic shock, etc.

Accordingly, another aspect of this invention provides a method of treating diseases or medical conditions in a mammal mediated by AKT protein kinases, comprising administering to said mammal one or more compounds of Formula I or a pharmaceutically acceptable salt or prodrug thereof in an amount effective to treat or prevent said disorder.

In the case of cancer, an effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

The amount of a compound of Formula I that will correspond to such an amount will vary depending upon factors such as the particular compound, disease condition and its severity, the identity (e.g., weight) of the mammal in need of treatment, but can nevertheless be routinely determined by one skilled in the art.

This invention also provides compounds of Formula I for use in the treatment of AKT protein kinase-mediated conditions.

An additional aspect of the invention is the use of a compound of Formula I in the preparation of a medicament for therapy, such as for the treatment or prevention of AKT protein kinase-mediated conditions.

Combination Therapy

The compounds of this invention and stereoisomers and pharmaceutically acceptable salts thereof may be employed alone or in combination with other therapeutic agents for treatment. The compounds of the present invention can be used in combination with one or more additional drugs, for example an anti-inflammatory compound that works by a different mechanism of action. The second compound of the pharmaceutical combination formulation or dosing regimen preferably has complementary activities to the compound of this invention such that they do not adversely affect each other. Such molecules are suitably present in combination in amounts that are effective for the purpose intended. The compounds may be administered together in a unitary pharmaceutical composition or separately and, when administered separately this may occur simultaneously or sequentially in any order. Such sequential administration may be close in time or remote in time.

Examples of chemotherapeutic agents include Erlotinib (TARCEVA®, Genentech, Inc./OSI Pharm.), Trastuzumab (HERCEPTIN®, Genentech, Inc.); bevacizumab (AVASTIN®, Genentech, Inc.); Rituximab (RITUXAN®, Genentech, Inc./Biogen Idec, Inc.), Bortezomib (VELCADE®, Millennium Pharm.), Fulvestrant (FASLODEX®, AstraZeneca), Sutent (SU11248, Pfizer), Letrozole (FEMARA®, Novartis), Imatinib mesylate (GLEEVEC®, Novartis), PTK787/ZK 222584 (Novartis), Oxaliplatin (Eloxatin®, Sanofi), 5-FU (5-fluorouracil), Leucovorin, Rapamycin (Sirolimus, RAPAMUNE®, Wyeth), Lapatinib (GSK572016, Glaxo Smith Kline), Lonafarnib (SCH 66336), Sorafenib (BAY43-9006, Bayer Labs), and Gefitinib (IRESSA®, AstraZeneca), AG1478, AG1571 (SU 5271; Sugen), alkylating agents such as thiotepa and CYTOXAN® cyclosphosphamide, ADRIAMYCIN® (doxorubicin), TAXOL® (paclitaxel; Bristol-Myers Squibb, Princeton, N.J.), ABRAXANE® (Cremophor-free), and TAXOTERE® (doxetaxel; Rhone-Poulenc Rorer, Antony, France).

Articles of Manufacture

In another embodiment of the invention, an article of manufacture, or "kit", containing materials useful for the treatment of the disorders described above is provided. In one embodiment, the kit comprises a container comprising a compound of this invention. Suitable containers include, for example, bottles, vials, syringes, blister pack, etc. The container may be formed from a variety of materials such as glass or plastic. The container may hold a compound of this invention or a formulation thereof which is effective for treating the condition and may have a sterile access port (for example, the container may be an intravenous solution bag or a vial having a stopper pierceable by a hypodermic injection needle).

The kit may further comprise a label or package insert on or associated with the container. In one embodiment, the label or package inserts indicates that the composition comprising a compound of this invention can be used to treat a disorder mediated, for example, by AKT kinase. The label or package insert may also indicate that the composition can be used to treat other disorders.

In certain embodiments, the kits are suitable for the delivery of solid oral forms of a compound of this invention, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to another embodiment, a kit may comprise (a) a first container with a compound of this invention contained therein; and (b) a second container with a second pharmaceutical formulation contained therein, wherein the second pharmaceutical formulation comprises a second compound useful for treating a disorder mediated by AKT kinase. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the compound of this invention and, if present, the second pharmaceutical formulation. For example, if the kit comprises a first composition comprising a compound of this invention and a second pharmaceutical formulation, the kit may further comprise directions for the simultaneous, sequential or separate administration of the first and second pharmaceutical compositions to a patient in need thereof.

In certain other embodiments wherein the kit comprises a composition of this invention and a second therapeutic agent, the kit may comprise a container for containing the separate compositions such as a divided bottle or a divided foil packet, however, the separate compositions may also be contained within a single, undivided container. In certain embodiments, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

Accordingly, a further aspect of this invention provides a kit for treating a disorder or disease mediated by Akt kinase, wherein said kit comprises a) a first pharmaceutical composition comprising a compound of this invention or a pharmaceutically acceptable salt thereof; and b) instructions for use.

In certain embodiments, the kit further comprises (c) a second pharmaceutical composition, wherein the second pharmaceutical composition comprises a second compound suitable for treating a disorder or disease mediated by Akt kinase. In certain embodiment comprising a second pharmaceutical composition, the kit further comprises instructions for the simultaneous, sequential or separate administration of said first and second pharmaceutical compositions to a patient in need thereof. In certain embodiments, said first and second pharmaceutical compositions are contained in separate containers. In other embodiments, said first and second pharmaceutical compositions are contained in the same container.

Although the compounds of Formula I are primarily of value as therapeutic agents for use in mammals, they are also useful whenever it is required to control AKT protein kinases, tyrosine kinases, additional serine/threonine kinases, and/or dual specificity kinases. Thus, they are useful as pharmacological standards for use in the development of new biological tests and in the search for new pharmacological agents.

The activity of the compounds of this invention may be assayed for AKT protein kinases, tyrosine kinases, additional serine/threonine kinases, and/or dual specificity kinases in vitro, in vivo, or in a cell line. In vitro assays include assays that determine inhibition of the kinase activity. Alternate in vitro assays quantitate the ability of the inhibitor to bind to kinases and may be measured either by radiolabelling the inhibitor prior to binding, isolating the inhibitor/kinase complex and determining the amount of radiolabel bound, or by running a competition experiment where new inhibitors are incubated with known radioligands. These and other useful in vitro and cell culture assays are well known to those of skill in the art.

Although the invention has been described and illustrated with a certain degree of particularity, it is understood that the present disclosure has been made only by way of example, and that numerous changes in the combination and arrangement of parts can be resorted to by those skilled in the art without departing from the spirit and scope of the invention, as hereinafter claimed.

BIOLOGICAL EXAMPLES

AKT-1 Kinase Assay

The activity of the compounds described in the present invention may be determined by the following kinase assay, which measures the phosphorylation of a fluorescently-labeled peptide by full-length human recombinant active AKT-1 by fluorescent polarization using a commercially available IMAP kit.

The assay materials are obtained from an IMAP AKT Assay Bulk Kit, product #R8059, from Molecular Devices, Sunnyvale, Calif. The kit materials include an IMAP Reaction Buffer (5×). The diluted 1×IMAP Reaction Buffer contained 10 mM Tris-HCl, pH 7.2, 10 mM $MgCl_2$, 0.1% BSA, 0.05% $NaN_3$. DTT is routinely added to a final concentration of 1 mM immediately prior to use. Also included is IMAP Binding Buffer (5×), and IMAP Binding Reagent. The Binding Solution is prepared as a 1:400 dilution of IMAP Binding Reagent into 1×IMAP Binding Buffer.

The fluorescein-labeled AKT Substrate (Crosstide) has the sequence (F1)-GRPRTSSFAEG. A stock solution of 20 µM is made up in 1×IMAP Reaction Buffer.

The plates used include a Costar 3657 (382-well made of polypropylene and having a white, v-bottom) that is used for compound dilution and for preparing the compound-ATP mixture. The assay plate is a Packard ProxyPlate™-384 F.

The AKT-1 used is made from full-length, human recombinant AKT-1 that is activated with PDK1 and MAP kinase 2.

To perform the assay, stock solutions of compounds at 10 mM in DMSO are prepared. The stock solutions and the control compound are serially diluted 1:2 nine times into DMSO (10 µL of compound+10 µL of DMSO) to give 50× dilution series over the desired dosing range. Next, 2.1-1 µL aliquots of the compounds in DMSO are transferred to a Costar 3657 plate containing 50 µL of 10.4 µM ATP in 1×IMAP Reaction Buffer containing 1 mM DTT. After thorough mixing, 2.5-4 aliquots are transferred to a Proxy-Plate™-384 F plate.

The assay is initiated by the addition of 2.5-4 aliquots of a solution containing 200 nM of fluorescently-labeled peptide substrate and 4 nM AKT-1. The plate is centrifuged for 1 minute at 1000 g and incubated for 60 minute at ambient temperature. The reaction is then quenched by the addition of 15 µL of Binding Solution, centrifuged again and incubated for an additional 30 minutes at ambient temperature prior to reading on a Victor 1420 Multilabel HTS Counter configured to measure fluorescence polarization.

The compounds of Examples 1-20 were tested in the above assay and found to have an $IC_{50}$ of less than 1 µM.

PREPARATIVE EXAMPLES

In order to illustrate the invention, the following examples are included. However, it is to be understood that these examples do not limit the invention and are only meant to suggest a method of practicing the invention. Persons skilled in the art will recognize that the chemical reactions described may be readily adapted to prepare a number of other compounds of the invention, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

In the Examples described below, unless otherwise indicated all temperatures are set forth in degrees Celsius. Reagents were purchased from commercial suppliers such as Sigma-Aldrich, Alfa Aesar, or TCI, and were used without further purification unless otherwise indicated. Tetrahydrofuran ("THF"), dichloromethane ("DCM"), toluene, and dioxane were purchased from Aldrich in Sure seal bottles and used as received.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

$^1$H NMR spectra were recorded on a Varian instrument operating at 400 MHz. $^1$H-NMR spectra were obtained as $CDCl_3$, $CD_3OD$, $D_2O$ or $d_6$-DMSO solutions (reported in ppm), using tetramethylsilane (0.00 ppm) or residual solvent ($CDCl_3$: 7.25 ppm; $CD_3OD$: 3.31 ppm; $D_2O$: 4.79 ppm; $d_6$-DMSO: 2.50 ppm) as the reference standard. When peak multiplicities are reported, the following abbreviations are used: s (singlet), d (doublet), t (triplet), q (quartet), m (multiplet), br (broadened), dd (doublet of doublets), dt (doublet of triplets). Coupling constants, when given, are reported in Hertz (Hz).

Example 1

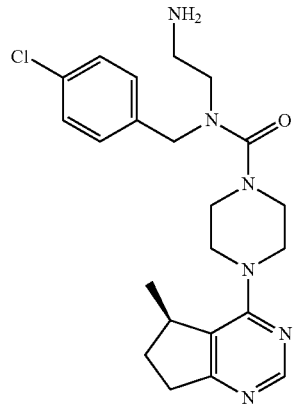 [SMILES: C[C@@H]1CCc2ncnc(N3CCN(C(=O)N(CCN)Cc4ccc(Cl)cc4)CC3)c21]

(R)—N-(2-aminoethyl)-N-(4-chlorobenzyl)-4-(5-methyl-6,7-dihydro-5H-cyclopenta[d]pyrimidin-4-yl)piperazine-1-carboxamide Step 1: Sodium triacetoxyborohydride (3.3 g, 15.4 mmol, 1.1 eq.) was added at room temperature to a solution of 4-chlorobenzaldehyde (2 g, 14 mmol), tert-butyl 2-aminoethylcarbamate (4.5 mL, 28.5 mmol, 1.2 eq.) and acetic acid (2.5 mL) in dichloroethane (20 mL). The reaction mixture was allowed to stir overnight before being quenched with 0.5M HCl (30 mL). The mixture was then extracted with dichloromethane one time and then brine was added. The precipitate was filtered and dried to give tert-butyl 2-(4-chlorobenzylamino)ethylcarbamate (3.58 g, 90%), MS (ESI) m/e (M+H$^+$) 285.

Step 2: Benzyl 4-(chlorocarbonyl)piperazine-1-carboxylate (233 mg, 0.83 mmol) was added at room temperature to a solution of tert-butyl 2-(4-chlorobenzylamino)ethylcarbamate (235 mg, 0.83 mmol) and Hunig's base (0.2 mL, 1.2 mmol, 1.5 eq.) in dichloromethane (1.6 mL). The reaction was allowed to stir overnight. The reaction mixture was then concentrated to the crude product, which was purified by flash column chromatography to afford benzyl 4-((2-(tert-butoxycarbonylamino)ethyl)(4-chlorobenzyl)carbamoyl)piperazine-1-carboxylate as foam (167 mg, 38%). MS (ESI) m/e (M+H$^+$) 531.

Step 3: A mixture of benzyl 4-((2-(tert-butoxycarbonylamino)ethyl)(4-chlorobenzyl)carbamoyl)piperazine-1-carboxylate (200 mg, 0.38 mmol) in a KOH/MeOH/H$_2$O (10 mL; prepared as a stock solution using 10 g KOH, 50 mL MeOH and 25 mL H$_2$O) solution of was stirred for 2 hours at 80° C. The reaction was extracted with EtOAc, dried over NaSO$_4$ and concentrated under reduced pressure to yield tert-butyl 2-(N-(4-chlorobenzyl)piperazine-1-carboxamido)ethylcarbamate (132 mg, 89%). MS (ESI) m/e (M+H$^+$) 397.

Step 4: (R)-(+)-Pulegone (76.12 g, 0.5 mmol), anhydrous NaHCO$_3$ (12.5 g) and anhydrous ether (500 mL) were added to a 1 L round-bottom flask. The reaction mixture was cooled with an ice-bath under nitrogen. Bromine (25.62 mL, 0.5 mmol) was added dropwise over 30 minutes. The mixture was filtered and carefully added to NaOEt (21%, 412 mL, 1.11 mmol) in an ice-cooled bath. The mixture was stirred at room temperature overnight, and then 5% HCl (1 L) and ether (300 mL) were added. The aqueous phase was extracted with ether (2×300 mL). The combined organic phase was washed with water, dried and concentrated. The residue was added to a warmed solution of semicarbazide hydrochloride (37.5 g) and NaOAc (37.5 g) in water (300 mL). Then boiling ethanol (300 mL) was added to give a clear solution. The mixture was refluxed for 2.5 hours and then stirred at room temperature overnight. The mixture was treated with water (1 L) and ether (300 mL). The aqueous phase was extracted with ether (2×300 mL). The combined organic phase was washed with water, dried and concentrated. The residue was purified by vacuum distillation (73-76° C. at 0.8 mm Hg) to give (2R)-ethyl 2-methyl-5-(propan-2-ylidene)cyclopentanecarboxylate (63 g, 64%). $^1$H NMR (CDCl$_3$, 400 MHz) δ 4.13 (m, 2H), 3.38 (d, J=16 Hz, 0.5H), 2.93 (m, 0.5H), 2.50-2.17 (m, 2H), 1.98 (m, 1H), 1.76 (m, 1H), 1.23 (m, 6H), 1.05 (m, 6H).

Step 5: (2R)-Ethyl 2-methyl-5-(propan-2-ylidene)cyclopentanecarboxylate (24 g, 0.122 mol) in ethyl acetate (100 mL) was cooled to −68° C. with dry ice/isopropanol. Ozonized oxygen (5-7 ft$^3$h$^{-1}$ of O$_2$) was bubbled through the solution for 3.5 hours. The reaction mixture was flushed with nitrogen at room temperature until the color disappeared. The ethyl acetate was removed under vacuum, and the residue was dissolved in acetic acid (150 mL) and cooled by ice water. Zinc powder (45 g) was then added. The solution was stirred for 30 minutes and then filtered. The filtrate was neutralized with 2N NaOH (1.3 L) and NaHCO$_3$. The aqueous phase was extracted with ether (3×200 mL). The organic phase was combined, washed with water, dried and concentrated to afford (2R)-ethyl 2-methyl-5-oxocyclopentanecarboxylate (20 g, 96%). $^1$H NMR (CDCl$_3$, 400 MHz) δ 4.21 (m, 2H), 2.77 (d, J=11.2 Hz, 1H), 2.60 (m, 1H), 2.50-2.10 (m, 3H), 1.42 (m, 1H), 1.33 (m, 3H), 1.23 (m, 3H).

Step 6: KOH (8.3 g, 147.9 mmol) in water (60 mL) was added to a solution of a mixture of (2R)-ethyl 2-methyl-5-oxocyclopentanecarboxylate (20 g, 117.5 mmol) and thiourea (9.2 g, 120.9 mmol) in ethanol (100 mL). The mixture was refluxed for 10 hours. After cooling, the solvent was removed, and the residue was neutralized with concentrated HCl (12 mL) at 0° C. The mixture was then extracted with DCM (3×150 mL). The solvent was removed, and the residue was purified by silica gel chromatography, eluting with hexane/ethyl acetate (2:1) to give (R)-2-mercapto-5-methyl-6,7-dihydro-5H-cyclopenta[d]pyrimidin-4-ol (12 g, 56%). MS (APCI+) [M+H]$^+$ 183.

Step 7: Raney Nickel (15 g) and NH$_4$OH (20 mL) were added to a suspension of (R)-2-mercapto-5-methyl-6,7-dihydro-5H-cyclopenta[d]pyrimidin-4-ol (12 g, 65.8 mmol) in distilled water (100 mL). The mixture was refluxed for 3 hours and then filtered. The filtrate was concentrated to afford (R)-5-methyl-6,7-dihydro-5H-cyclopenta[d]pyrimidin-4-ol (9.89 g, 99%). MS (APCI+) [M+H]$^+$ 151.

Step 8: A mixture of (R)-5-methyl-6,7-dihydro-5H-cyclopenta[d]pyrimidin-4-ol (5.8 g, 38.62 mmol) in POCl$_3$ (20 mL) was refluxed for 5 minutes. Excess POCl$_3$ was removed under vacuum, and the residue was dissolved in DCM (50 mL). The mixture was then added to saturated NaHCO$_3$ (200 mL). The aqueous phase was extracted with DCM (3×100 mL), and the combined organic phases were dried and concentrated. The residue was purified by silica gel chromatography, eluting with ethyl acetate to give (R)-4-chloro-5-methyl-6,7-dihydro-5H-cyclopenta[d]pyrimidine (3.18 g, 49%). $^1$H NMR (CDCl$_3$, 400 MHz) δ 8.81 (s, 1H), 3.47 (m, 1H), 3.20 (m, 1H), 3.05 (m, 1H), 2.41 (m, 1H), 1.86 (m, 3H), 1.47 (m, 3H).

Step 9: (R)-4-Chloro-5-methyl-6,7-dihydro-5H-cyclopenta[d]pyrimidine (46 mg, 0.27 mmol, 1.1 eq.) was added to a solution of the tert-butyl 2-(N-(4-chlorobenzyl)piperazine-1-carboxamido)ethylcarbamate (100 mg, 0.25 mmol) and Hunig's base (0.1 mL, 0.75 mmol, 3 eq.) in acetonitrile (3 mL). The resulting mixture was heated to 80° C. overnight. The reaction mixture was diluted with H$_2$O and extracted with DCM, dried and concentrated to yield (R)-tert-butyl 2-(N-(4-chlorobenzyl)-4-(5-methyl-6,7-dihydro-5H-cyclopenta[d]pyrimidin-4-yl)piperazine-1-carboxamido)ethylcarbamate (40 mg, 30%). MS (ESI) m/e (M+H$^+$) 529.

Step 10: A solution of HCl/dioxane at 0° C. was added to (R)-tert-butyl 2-(N-(4-chlorobenzyl)-4-(5-methyl-6,7-dihydro-5H-cyclopenta[d]pyrimidin-4-yl)piperazine-1-carboxamido)ethylcarbamate (40 mg, 0.075 mmol) in MeOH (1 mL). The reaction mixture was stirred at 25° C. for 1 hour. After removal of the solvent, the crude product was purified by preparative HPLC to afford (R)—N-(2-aminoethyl)-N-(4-chlorobenzyl)-4-(5-methyl-6,7-dihydro-5H-cyclopenta[d]pyrimidin-4-yl)piperazine-1-carboxamide (32 mg, 90%). MS (ESI) m/e (M+H$^+$) 429.2. $^1$H NMR: δ=8.56 (s, 1H), δ=7.23-7.56 (dd, 4H), δ=4.51 (s, 2H), δ=3.97-4.19 (m, 4H), δ=3.70 (m, 1H), δ=3.61 (m, 4H), δ=3.40-3.43 (t, 2H), δ=2.96-3.15 (m, 4H), δ=2.42 (m, 1H), δ=1.89 (m, 1H), δ=1.21-1.22 (d, 3H).

Example 2

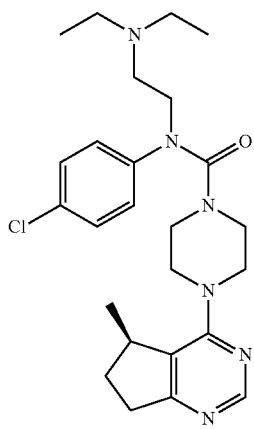 [SMILES: CCN(CC)CCN(C(=O)N1CCN(c2ncnc3c2[C@H](C)CC3)CC1)c1ccc(Cl)cc1]

(R)—N-(4-chlorophenyl)-N-(2-(diethylamino)ethyl)-4-(5-methyl-6,7-dihydro-5H-cyclopenta[d]pyrimidin-4-yl)piperazine-1-carboxamide Step 1: Ethyl pulegenate (130 g, 662 mmol) in EtOAc (900 mL) was cooled to −78° C. using a dry ice-isopropanol bath. This mixture was subjected to ozonolysis until the reaction turned purple in color. At this point, ozone generation ceased, and the reaction was removed from the dry-ice bath. Oxygen was bubbled through the reaction mixture until it turned yellow. The reaction mixture was concentrated under vacuum, and the resulting residue was dissolved in glacial acetic acid (400 mL). The solution was cooled to 0° C., and Zn dust (65 g, 993 mmol) was added portionwise over 30 minutes. The reaction was then allowed to stir for 2 hours, at which point the reaction mixture was filtered through a pad of celite to remove the zinc dust. The acetic acid was neutralized to a pH of 7 with aqueous NaOH and NaHCO$_3$ and extracted with ether (3×800 mL). The combined organics were dried with brine, MgSO$_4$ and concentrated to give (2R)-ethyl 2-methyl-5-oxocyclopentanecarboxylate as a liquid (107 g, 95%).

Step 2: Ammonium acetate (240.03 g, 3113.9 mmol) was added to a solution of (R)-ethyl 2-methyl-5-oxocyclopentanecarboxylate (106.0 g, 622.78 mmol) in MeOH (1.2 L). The reaction mixture was stirred at room temperature under nitrogen for 20 hours, after which it was complete as judged by TLC and HPLC. The reaction mixture was concentrated to remove MeOH. The resulting residue was dissolved in DCM, washed twice with H$_2$O, once with brine, dried (Na$_2$SO$_4$), filtered, and concentrated to give (R)-ethyl 2-amino-5-methylcyclopent-1-enecarboxylate (102 g, 97% yield) as an oil. LC/MS (APCI+) m/z 170 [M+H]$^+$.

Step 3: A solution containing (R)-ethyl 2-amino-5-methylcyclopent-1-enecarboxylate (161.61 g, 955.024 mmol) and ammonium formate (90.3298 g, 1432.54 mmol) in formamide (303.456 ml, 7640.19 mmol) was heated to an internal temperature of 150° C. and stirred for 17 hours. The reaction mixture was cooled, and transferred to a 2 L single nextracted flask. Then excess formamide was removed by high vacuum distillation. Once formamide stopped coming over, the remaining oil in the still pot was dissolved in DCM and washed with brine (3×200 mL). The combined aqueous washes were extracted with DCM. The combined organic extracts were dried (Na$_2$SO$_4$), filtered, and concentrated. The resulting brown oil was dissolved in minimal DCM, and this solution was added using a separatory funnel to a stirred solution of ether (ca. 5 vol of ether vs. DCM solution), causing some brown precipitate to form. This brown precipitate was removed by filtration through a medium frit funnel which was rinsed with ether and disposed. The filtrate was concentrated, the trituration from ether repeated two more times and then dried on high vacuum line to give (R)-5-methyl-6,7-dihydro-5H-cyclopenta[d]pyrimidin-4-ol (93.225 g, 65.00% yield) as a pasty solid. LC/MS (APCI−) m/z 149.2.

Step 4: Neat POCl$_3$ (463.9 ml, 5067 mmol) was added slowly by addition funnel to a 0° C. solution of (R)-5-methyl-6,7-dihydro-5H-cyclopenta[d]pyrimidin-4-ol (152.2 g, 1013 mmol) in DCE (1.2 L). After the addition was complete, the reaction mixture was warmed to room temperature, then heated to reflux and stirred for 70 minutes. The reaction was complete as determined by HPLC. The reaction mixture was cooled to room temperature, and the excess POCl$_3$ was quenched in 4 portions as follows: Reaction mixture transferred to separatory funnel and dripped into a beaker containing ice and saturated NaHCO$_3$ solution cooled in an ice bath. Once the addition of each portion of the reaction mixture was completed, the quenched mixture was stirred for 30 minutes to ensure complete destruction of POCl$_3$ prior to transfer to separatory funnel. The mixture was transferred to the separatory funnel and extracted twice with DCM. The combined extracts were dried (Na$_2$SO$_4$), filtered, and concentrated. The crude was purified on silica gel as follows: silica gel (1 kg) was slurried in 9:1 hexane:ethyl acetate onto a 3 L fritted funnel, silica settled under vacuum, topped with sand. The crude was loaded with a DCM/hexane mixture, and the compound was eluted using 1 L sidearm flasks under vacuum. High Rf byproducts eluted first, then (R)-4-chloro-5-methyl-6,7-dihydro-5H-cyclopenta[d]pyrimidine (104.4 g, 61.09% yield) as an oil.

Step 5: 4-Chloro-aniline (0.5 g, 3.9 mmol) was added to a solution of 2-bromo-N,N-diethylethylamine hydrobromide (1.12 g, 4.3 mmol) and N,N-diisopropylethylamine (2 mL, 11.7 mmol) in toluene (7.8 mL). The mixture was stirred at room temperature for 5 hours. The mixture was then diluted with EtOAc (30 mL) and saturated NaHCO$_3$ (20 mL). The organic layer was washed with H$_2$O (1×20 mL), dried (Na$_2$SO$_4$), filtered and concentrated to give 4-chloro-N-(2-(diethylamino)ethyl)benzenamine as an oil which was used without purification. MS (APCI+) [M+H]$^+$ 227.3.

Step 6: tert-Butyl 4-chlorocarbonyl-piperazine-1-carboxylate (0.97 g, 3.9 mmol) was added to a solution of 4-chloro-N-(2-(diethylamino)ethyl)benzenamine (884 mg, 3.9 mmol) and N,N-diisopropylethylamine (1.9 mL, 11.7 mmol) in DCM (8 mL). The reaction mixture was heated at reflux for 20 hours. The mixture was cooled to room temperature, quenched with saturated NH$_4$Cl (10 mL), and extracted with DCM (2×20 mL). The combined organics were dried (Na$_2$SO$_4$) and concentrated. The crude product was purified by silica gel chromatography to give tert-butyl 4-(N-(4-chlorophenyl)-N-(2-(diethylamino)ethyl)carbamoyl)piperazine-1-carboxylate (311 mg, 18%). MS (APCI+) [M+H]$^+$ 439.4. $^1$H NMR (CDCl$_3$, 400 MHz) δ 7.29 (d, J=8.8 Hz, 2H), 7.09 (d, J=8.8 Hz, 2H), 3.70-3.66 (m, 2H), 3.45-3.42 (m, 2H), 3.24-3.21 (m, 4H), 3.15-3.12 (m, 2H), 2.61-2.57 (m, 2H), 2.52 (q, J=7.2 Hz, 4H), 1.42 (s, 9H), 0.99 (t, J=7.2 Hz, 6H).

Step 7: Trifluoroacetic acid (1 mL) was added to a solution of tert-butyl 4-(N-(4-chlorophenyl)-N-(2-(diethylamino)

ethyl)carbamoyl)piperazine-1-carboxylate (311 mg, 0.7 mmol) in DCM (5 mL). The mixture was stirred at room temperature for 3 hours, and then concentrated in vacuo. The residue was dissolved in n-butanol (2 mL). N,N-Diisopropylethylamine (0.5 mL, 3.6 mmol) was added followed by (R)-4-chloro-6,7-dihydro-5-methyl-5H-cyclopenta[d]pyrimidine (113 mg, 0.84 mmol). The reaction mixture was heated at 80° C. for 16 hours. The mixture was then diluted with H$_2$O, and extracted with DCM (2×20 mL). The combined organics were dried (Na$_2$SO$_4$), filtered and concentrated. The crude product was purified by preparative HPLC to give N-(4-chlorophenyl)-N-(2-(diethylamino)ethyl)-4-((R)-6,7-dihydro-5-methyl-5H-cyclopenta[d]pyrimidin-4-yl)piperazine-1-carboxamide (39.9 mg, 12%). MS (APCI+) [M+H]$^+$ 471.3. $^1$H NMR (CDCl$_3$, 400 MHz) δ☐: 8.49 (s, 1H), 7.40-7.35 (m, 2H), 7.17-7.13 (m, 2H), 4.06-3.95 (m, 4H), 3.77-3.70 (m, 2H), 3.51-3.44 (m, 1H), 3.39-3.02 (m, 11H), 2.42-2.32 (m, 1H), 1.88-1.82 (m, 1H), 1.33 (t, J=7.2 Hz, 6H), 1.15 (d, J=6.8 Hz, 3H).

Example 3

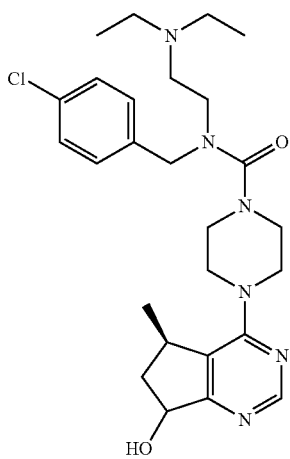 [SMILES: CCN(CC)CCN(Cc1ccc(Cl)cc1)C(=O)N1CCN(c2ncnc3c2[C@H](C)CC3O)CC1]

N-(4-chlorobenzyl)-N-(2-(diethylamino)ethyl)-4-((5R)-7-hydroxy-5-methyl-6,7-dihydro-5H-cyclopenta[d]pyrimidin-4-yl)piperazine-1-carboxamide Step 1: (R)-(+)-Pulegone (76.12 g, 0.5 mmol), anhydrous NaHCO$_3$ (12.5 g) and anhydrous ether (500 mL) were added to a 1 L round-bottom flask. The reaction mixture was cooled with an ice-bath under nitrogen. Bromine (25.62 mL, 0.5 mmol) was added dropwise over 30 minutes. The mixture was filtered and carefully added to NaOEt (21%, 412 mL, 1.11 mmol) in an ice-cooled bath. The mixture was stirred at room temperature overnight, and then 5% HCl (1 L) and ether (300 mL) were added. The aqueous phase was extracted with ether (2×300 mL). The combined organic phase was washed with water, dried and concentrated. The residue was added to a warmed solution of semicarbazide hydrochloride (37.5 g) and NaOAc (37.5 g) in water (300 mL), and then boiling ethanol (300 mL) was added to give a clear solution. The mixture was refluxed for 2.5 hours and then stirred at room temperature overnight. The mixture was treated with water (1 L) and ether (300 mL). The aqueous phase was extracted with ether (2×300 mL). The combined organic phase was washed with water, dried and concentrated. The residue was purified by vacuum distillation (73-76° C. at 0.8 mm Hg) to give (2R)-ethyl 2-methyl-5-(propan-2-ylidene)cyclopentanecarboxylate (63 g, 64%). $^1$H NMR (CDCl$_3$, 400 MHz) δ 4.13 (m, 2H), 3.38 (d, J=16 Hz, 0.5H), 2.93 (m, 0.5H), 2.50-2.17 (m, 2H), 1.98 (m, 1H), 1.76 (m, 1H), 1.23 (m, 6H), 1.05 (m, 6H).

Step 2: (2R)-Ethyl 2-methyl-5-(propan-2-ylidene)cyclopentanecarboxylate (24 g, 0.122 mol) in ethyl acetate (100 mL) was cooled to −68° C. with dry ice/isopropanol. Ozonized oxygen (5-7 ft$^3$h$^1$ of O$_2$) was bubbled through the solution for 3.5 hours. The reaction mixture was flushed with nitrogen at room temperature until the color disappeared. The ethyl acetate was removed under vacuum, and the residue was dissolved in acetic acid (150 mL) and cooled by ice water. Zinc powder (45 g) was then added. The solution was stirred for 30 minutes and then filtered. The filtrate was neutralized with 2N NaOH (1.3 L) and NaHCO$_3$. The aqueous phase was extracted with ether (3×200 mL). The organic phase was combined, washed with water, dried and concentrated to afford (2R)-ethyl 2-methyl-5-oxocyclopentanecarboxylate (20 g, 96%). $^1$H NMR (CDCl$_3$, 400 MHz) δ 4.21 (m, 2H), 2.77 (d, J=11.2 Hz, 1H), 2.60 (m, 1H), 2.50-2.10 (m, 3H), 1.42 (m, 1H), 1.33 (m, 3H), 1.23 (m, 3H).

Step 3: KOH (8.3 g, 147.9 mmol) in water (60 mL) was added to a solution of a mixture of (2R)-ethyl 2-methyl-5-oxocyclopentanecarboxylate (20 g, 117.5 mmol) and thiourea (9.2 g, 120.9 mmol) in ethanol (100 mL). The mixture was refluxed for 10 hours. After cooling, the solvent was removed and the residue was neutralized with concentrated HCl (12 mL) at 0° C. and then extracted with DCM (3×150 mL). The solvent was removed, and the residue was purified by silica gel chromatography, eluting with hexane/ethyl acetate (2:1) to give (R)-2-mercapto-5-methyl-6,7-dihydro-5H-cyclopenta[d]pyrimidin-4-ol (12 g, 56%). MS (APCI+) [M+H]$^+$ 183.

Step 4: Raney Nickel (15 g) and NH$_4$OH (20 mL) was added to a suspension of (R)-2-mercapto-5-methyl-6,7-dihydro-5H-cyclopenta[d]pyrimidin-4-ol (12 g, 65.8 mmol) in distilled water (100 mL). The mixture was refluxed for 3 hours and then filtered. The filtrate was concentrated to afford (R)-5-methyl-6,7-dihydro-5H-cyclopenta[d]pyrimidin-4-ol (9.89 g, 99%). MS (APCI+) [M+H]$^+$ 151.

Step 5:
A mixture of (R)-5-methyl-6,7-dihydro-5H-cyclopenta[d]pyrimidin-4-ol (5.8 g, 38.62 mmol) in POCl$_3$ (20 mL) was refluxed for 5 minutes. The excess POCl$_3$ was removed under vacuum, and the residue was dissolved in DCM (50 mL). The mixture was then added to saturated NaHCO$_3$ (200 mL). The aqueous phase was extracted with DCM (3×100 mL), and the combined organic phases were dried and concentrated. The residue was purified by silica gel chromatography, eluting with ethyl acetate to give (R)-4-chloro-5-methyl-6,7-dihydro-5H-cyclopenta[d]pyrimidine (3.18 g, 49%). $^1$H NMR (CDCl$_3$, 400 MHz) δ 8.81 (s, 1H), 3.47 (m, 1H), 3.20 (m, 1H), 3.05 (m, 1H), 2.41 (m, 11H), 1.86 (m, 3H), 1.47 (m, 3H).

Step 6: m-CPBA (8.30 g, 37.0 mmol) was added in three portions to a solution of (R)-4-chloro-5-methyl-6,7-dihydro-5H-cyclopenta[d]pyrimidine (2.5 g, 14.8 mmol) in CHCl$_3$ (60 mL). The mixture was stirred at room temperature for 2 days. The mixture was cooled to 0° C., and Na$_2$S$_2$O$_3$ (10 g) in water (60 mL) was added dropwise. Na$_2$CO$_3$ (6 g) in water (20 mL) was then added. The reaction mixture was stirred for 20 minutes. The aqueous phase was extracted with CHCl$_3$ (2×200 mL), and the combined organic phases were concentrated at low temperature (<25° C.). The residue was purified by silica gel chromatography, eluting with ethyl acetate-DCM/MeOH (20:1) to give (R)-4-chloro-5-methyl-6,7-dihydro-5H-cyclopenta[d]pyrimidine-oxide (1.45 g, 53%). $^1$H NMR (CDCl₃, 400 MHz) δ 8.66 (s, 1H), 3.50 (m, 1H), 3.20 (m, 2H), 2.44 (m, 1H), 1.90 (m, 1H), 1.37 (d, J=7.2 Hz, 3H).

Step 7: A solution of (R)-4-chloro-5-methyl-6,7-dihydro-5H-cyclopenta[d]pyrimidine-oxide (1.45 g, 7.85 mmol) in acetic anhydride (20 mL) was heated to 110° C. for 2 hours. After cooling, excess solvent was removed under vacuum. The residue was purified by silica gel chromatography, eluting with hexane/ethyl acetate (3:1) to give (5R)-4-chloro-5-methyl-6,7-dihydro-5H-cyclopenta[d]pyrimidin-7-yl acetate (1.25 g, 70%). ¹H NMR (CDCl₃, 400 MHz) δ 8.92 (m, 1H), 6.30-6.03 (m, 1H), 3.60-3.30 (m, 1H), 2.84 (m, 1H), 2.40-2.20 (m, 1H), 2.15 (d, J=6 Hz, 2H), 1.75 (m, 2H), 1.47 (d, J=6.8, 2H), 1.38 (d, J=7.2, 1H). MS (APCI+) [M+H]⁺ 227.

Step 8: (5R)-4-Chloro-5-methyl-6,7-dihydro-5H-cyclopenta[d]pyrimidin-7-yl acetate was converted into (5R)-4-chloro-6,7-dihydro-5-methyl-5H-cyclopenta[d]pyrimidin-7-ol by treatment with LiOH in H₂O/THF, followed by an acidic workup (2N HCl in water) to remove the acetate group.

Step 9: 4-Chlorobenzylamine (1.0 mL, 8.2 mmol) was added to a solution of 2-bromo-N,N-diethylethylamine hydrobromide (2.4 g, 9.0 mmol) and triethylamine (3.4 mL, 25 mmol) in dichloromethane (16 mL). The mixture was stirred at room temperature for 5 hours. The mixture was then concentrated to give N1-(4-chlorobenzyl)-N2,N2-diethylethane-1,2-diamine as an oil which was used immediately without purification.

Step 10: tert-Butyl 4-chlorocarbonyl-piperazine-1-carboxylate (245 mg, 0.99 mmol) was added to a solution of N1-(4-chlorobenzyl)-N2,N2-diethylethane-1,2-diamine (235 mg, 0.98 mmol) and N,N-diisopropylethylamine (0.54 mL, 2.94 mmol) in DCM (2 mL). The reaction mixture was allowed to stir at room temperature for 1 hour. The mixture was quenched with saturated NH₄Cl (2 mL) and extracted with DCM (2×5 mL). The combined organics were dried (Na₂SO₄), filtered and concentrated. The crude product was purified by silica gel chromatography to give tert-butyl 4-(N-(4-chlorobenzyl)-N-(2-(diethylamino)ethyl)carbamoyl)piperazine-1-carboxylate (200 mg, 45%). ¹H NMR (CDCl₃, 400 MHz) δ 7.32 (d, J=8.4 Hz, 2 H), 7.19 (d, J=8.4 Hz, 2 H), 4.42 (s, 2 H), 3.45-3.40 (m, 4 H), 3.25-3.20 (m, 4 H), 3.18 (t, J=6.8 Hz, 2 Hz), 2.56 (t, J=6.8 Hz, 2 H), 2.49 (q, J=7.2 Hz, 4 H), 1.46 (s, 9 H), 0.99 (t, J=7.2 Hz, 6 H).

Step 11: Trifluoroacetic acid (1 mL) was added to a solution of tert-butyl 4-(N-(4-chlorobenzyl)-N-(2-(diethylamino)ethyl)carbamoyl)piperazine-1-carboxylate (88 mg, 0.19 mmol) in DCM (1 mL). The mixture was stirred at room temperature for 3 hours, and then concentrated in vacuo. The residue was dissolved in n-butanol (1 mL). N,N-diisopropylethylamine (0.11 mL, 0.6 mmol) was added to the solution. Then, (5R)-4-chloro-6,7-dihydro-5-methyl-5H-cyclopenta[d]pyrimidin-7-ol (37 mg, 0.20 mmol) was added to the solution. The reaction mixture was heated at 80° C. for 16 hours. The mixture was then diluted with H₂O (1 mL), and extracted with DCM (2×5 mL). The combined organics were dried (Na₂SO₄), filtered and concentrated. The crude product was purified by preparative HPLC to give N-(4-chlorobenzyl)-N-(2-(diethylamino)ethyl)-4-((5R)-6,7-dihydro-7-hydroxy-5-methyl-5H-cyclopenta[d]pyrimidin-4-yl)piperazine-1-carboxamide (19.9 mg, 21%). MS (APCI+) [M+H]⁺ 501.3. ¹H NMR (CDCl₃, 400 MHz) δ 8.46 (s, 1 H), 7.34 (d, J=8.4 Hz, 4 H), 7.13 (d, J=8.4 Hz, 4 H), 5.50 (t, J=8 Hz, 1 H), 5.28 (dd, J=3.6, 8.4 Hz, 1 H), 4.45 (s, 4 H), 4.14-4.04 (m, 4 H), 3.94-3.81 (m, 4 H), 3.51-3.42 (m, 8 H), 3.20-3.00 (m, 16 H), 2.73-2.64 (m, 2 H), 2.40-2.20 (m, 4 H), 2.05-1.98 (m, 1H), 1.86-1.78 (m, 1 H), 1.33 (d, J=7.2 Hz, 3 Hz), 1.28 (t, J=7.2 Hz, 12 H), 1.21 (d, J=6.8 Hz, 3 Hz).

Examples 4-14 shown in Table 1 can also be made according to the above described methods.

TABLE 1

| Example | Structure | Name | LCMS |
|---|---|---|---|
| 4 | 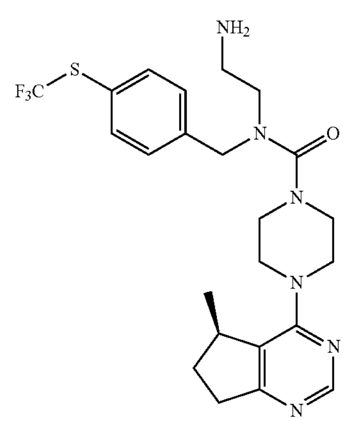 [SMILES: C[C@@H]1CCc2ncnc(N3CCN(C(=O)N(CCN)Cc4ccc(SC(F)(F)F)cc4)CC3)c21] | (R)-N-(2-aminoethyl)-4-(5-methyl-6,7-dihydro-5H-cyclopenta[d]pyrimidin-4-yl)-N-(4-(trifluoromethylthio)benzyl)piperazine-1-carboxamide | 495 |

TABLE 1-continued

| Example | Structure | Name | LCMS |
|---|---|---|---|
| 5 | 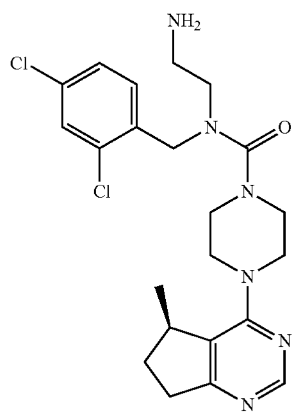 [SMILES: C[C@@H]1CCc2ncnc(N3CCN(C(=O)N(CCN)Cc4ccc(Cl)cc4Cl)CC3)c21] | (R)-N-(2-aminoethyl)-N-(2,4-dichlorobenzyl)-4-(5-methyl-6,7-dihydro-5H-cyclopenta[d]pyrimidin-4-yl)piperazine-1-carboxamide | 463.1 |
| 6 | 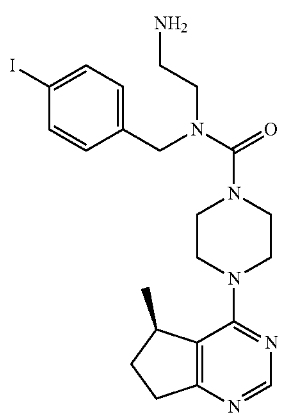 [SMILES: C[C@@H]1CCc2ncnc(N3CCN(C(=O)N(CCN)Cc4ccc(I)cc4)CC3)c21] | (R)-N-(2-aminoethyl)-N-(4-iodobenzyl)-4-(5-methyl-6,7-dihydro-5H-cyclopenta[d]pyrimidin-4-yl)piperazine-1-carboxamide | 521.1 |
| 7 | 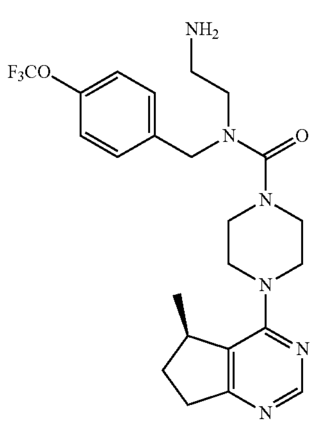 [SMILES: C[C@@H]1CCc2ncnc(N3CCN(C(=O)N(CCN)Cc4ccc(OC(F)(F)F)cc4)CC3)c21] | (R)-N-(2-aminoethyl)-4-(5-methyl-6,7-dihydro-5H-cyclopenta[d]pyrimidin-4-yl)-N-(4-(trifluoromethoxy)benzyl)piperazine-1-carboxamide | 479.2 |

TABLE 1-continued

| Example | Structure | Name | LCMS |
|---|---|---|---|
| 8 | 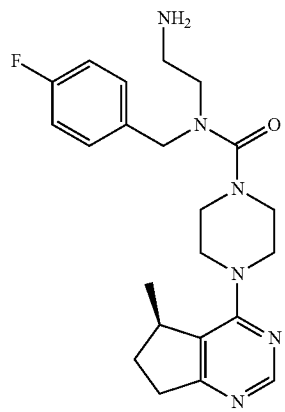 [SMILES: C[C@@H]1CCc2ncnc(N3CCN(C(=O)N(CCN)Cc4ccc(F)cc4)CC3)c21] | (R)-N-(2-aminoethyl)-N-(4-fluorobenzyl)-4-(5-methyl-6,7-dihydro-5H-cyclopenta[d]pyrimidin-4-yl)piperazine-1-carboxamide | 413.2 |
| 9 | 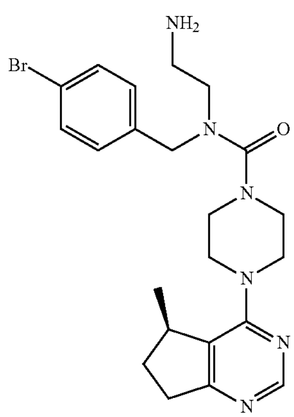 [SMILES: C[C@@H]1CCc2ncnc(N3CCN(C(=O)N(CCN)Cc4ccc(Br)cc4)CC3)c21] | (R)-N-(2-aminoethyl)-N-(4-bromobenzyl)-4-(5-methyl-6,7-dihydro-5H-cyclopenta[d]pyrimidin-4-yl)piperazine-1-carboxamide | 473.1 |
| 10 | 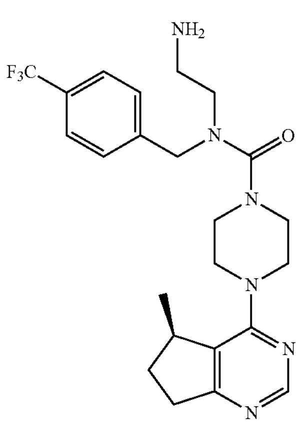 [SMILES: C[C@@H]1CCc2ncnc(N3CCN(C(=O)N(CCN)Cc4ccc(C(F)(F)F)cc4)CC3)c21] | (R)-N-(2-aminoethyl)-4-(5-methyl-6,7-dihydro-5H-cyclopenta[d]pyrimidin-4-yl)-N-(4-(trifluoromethyl)benzyl)piperazine-1-carboxamide | 463 |

TABLE 1-continued

| Example | Structure | Name | LCMS |
|---|---|---|---|
| 11 | 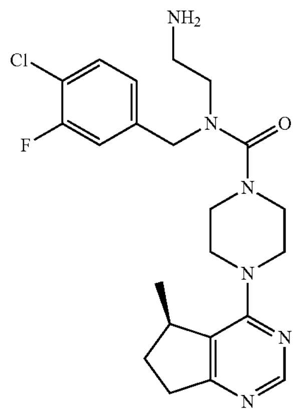 [SMILES: C[C@@H]1CCc2ncnc(N3CCN(C(=O)N(CCN)Cc4ccc(Cl)c(F)c4)CC3)c21] | (R)-N-(2-aminoethyl)-N-(4-chloro-3-fluorobenzyl)-4-(5-methyl-6,7-dihydro-5H-cyclopenta[d]pyrimidin-4-yl)piperazine-1-carboxamide | 447.1 |
| 12 | 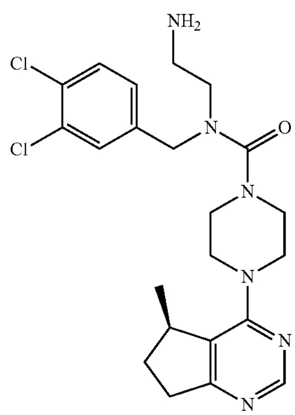 [SMILES: C[C@@H]1CCc2ncnc(N3CCN(C(=O)N(CCN)Cc4ccc(Cl)c(Cl)c4)CC3)c21] | (R)-N-(2-aminoethyl)-N-(3,4-dichlorobenzyl)-4-(5-methyl-6,7-dihydro-5H-cyclopenta[d]pyrimidin-4-yl)piperazine-1-carboxamide | 463.1 |
| 13 | 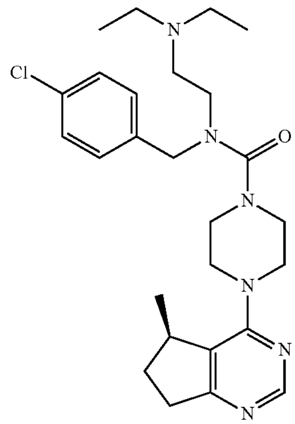 [SMILES: CCN(CC)CCN(Cc1ccc(Cl)cc1)C(=O)N1CCN(c2ncnc3c2[C@H](C)CC3)CC1] | (R)-N-(4-chlorobenzyl)-N-(2-(diethylamino)ethyl)-4-(5-methyl-6,7-dihydro-5H-cyclopenta[d]pyrimidin-4-yl)piperazine-1-carboxamide | 485.3 |

TABLE 1-continued

| Example | Structure | Name | LCMS |
|---|---|---|---|
| 14 | 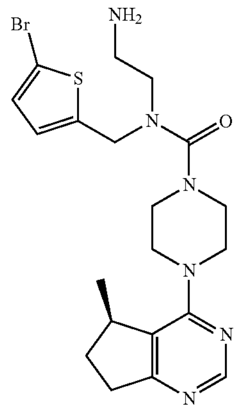 [SMILES: C[C@@H]1CCc2ncnc(N3CCN(C(=O)N(CCN)Cc4ccc(Br)s4)CC3)c21] | (R)-N-(2-aminoethyl)-N-((5-bromothiophen-2-yl)methyl)-4-(5-methyl-6,7-dihydro-5H-cyclopenta[d]pyrimidin-4-yl)piperazine-1-carboxamide | 479 |
| 15 | 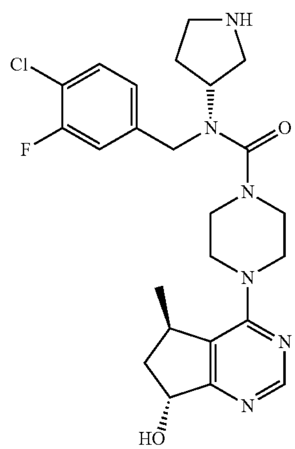 | N-(4-chloro-3-fluorobenzyl)-4-((5R,7R)-7-hydroxy-5-methyl-6,7-dihydro-5H-cyclopenta[d]pyrimidin-4-yl)-N-((R)-pyrrolidin-3-yl)piperazine-1-carboxamide | 489.2 |
| 16 | 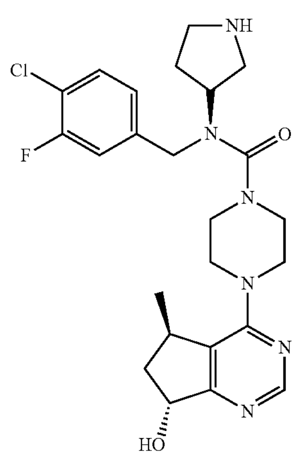 | N-(4-chloro-3-fluorobenzyl)-4-((5R,7R)-7-hydroxy-5-methyl-6,7-dihydro-5H-cyclopenta[d]pyrimidin-4-yl)-N-((S)-pyrrolidin-3-yl)piperazine-1-carboxamide | 489.2 |

TABLE 1-continued

| Example | Structure | Name | LCMS |
|---|---|---|---|
| 17 | 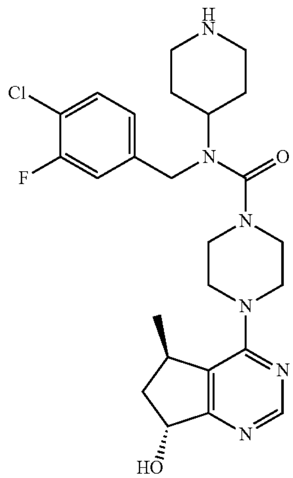 [SMILES: C[C@@H]1C[C@@H](O)c2ncnc(N3CCN(C(=O)N(Cc4ccc(Cl)c(F)c4)C4CCNCC4)CC3)c21] | N-(4-chloro-3-fluorobenzyl)-4-((5R,7R)-7-hydroxy-5-methyl-6,7-dihydro-5H-cyclopenta[d]pyrimidin-4-yl)-N-(piperidin-4-yl)piperazine-1-carboxamide | 503.2 |
| 18 | 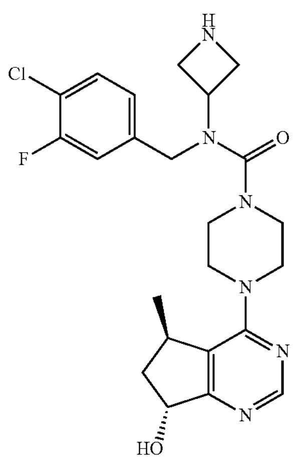 [SMILES: C[C@@H]1C[C@@H](O)c2ncnc(N3CCN(C(=O)N(Cc4ccc(Cl)c(F)c4)C4CNC4)CC3)c21] | N-(azetidin-3-yl)-N-(4-chloro-3-fluorobenzyl)-4-((5R,7R)-7-hydroxy-5-methyl-6,7-dihydro-5H-cyclopenta[d]pyrimidin-4-yl)piperazine-1-carboxamide | 475.2 |
| 19 | 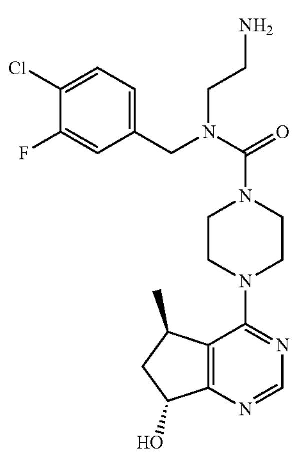 [SMILES: C[C@@H]1C[C@@H](O)c2ncnc(N3CCN(C(=O)N(CCN)Cc4ccc(Cl)c(F)c4)CC3)c21] | N-(2-aminoethyl)-N-(4-chloro-3-fluorobenzyl)-4-((5R,7R)-7-hydroxy-5-methyl-6,7-dihydro-5H-cyclopenta[d]pyrimidin-4-yl)piperazine-1-carboxamide | 463.2 |

TABLE 1-continued

| Example | Structure | Name | LCMS |
|---|---|---|---|
| 20 | 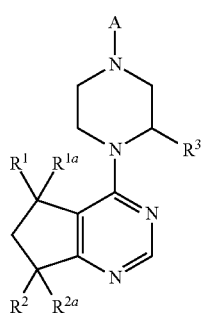 | N-(4-chloro-3-fluorobenzyl)-4-((5R,7R)-7-hydroxy-5-methyl-6,7-dihydro-5H-cyclopenta[d]pyrimidin-4-yl)-N-(2-(isopropylamino)ethyl)piperazine-1-carboxamide | 505.3 |

While the invention has been described in conjunction with the enumerated embodiments, it will be understood that they are not intended to limit the invention to those embodiments. On the contrary, the invention is intended to cover all alternatives, modifications and equivalents, which may be included within the scope of the present invention as defined by the claims. Thus, the foregoing description is considered as illustrative only of the principles of the invention.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

What is claimed is:

1. A method of treating a hyperproliferative disease or disorder in a mammal that is mediated by Akt signaling, said method comprising administering to said mammal an effective amount of a compound of Formula I:

I or an enantiomer or a pharmaceutically acceptable salt thereof, wherein:
$R^1$ and $R^{1a}$ are independently selected from H, Me, Et, vinyl, $CF_3$, $CHF_2$ or $CH_2F$;
$R^2$ is H, OH, OMe or F;
$R^{2a}$ is H, Me or F;
$R^3$ is H, Me, Et, or $CF_3$;

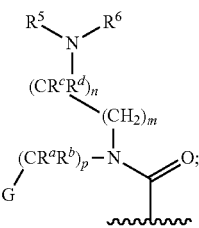

A is
G is phenyl optionally substituted by one to four $R^e$ groups or a 5-6 membered heteroaryl optionally substituted by a halogen;
$R^5$ and $R^6$ are independently H, $OCH_3$, $C_3$-$C_6$-cycloalkyl optionally substituted with F, OH, $C_1$-$C_3$ alkyl or $O(C_1$-$C_3$ alkyl), 4-6 membered heterocycle optionally substituted with F, OH, $C_1$-$C_3$ alkyl, cyclopropylmethyl or C(=O)($C_1$-$C_3$ alkyl), or $C_1$-$C_6$-alkyl optionally substituted with one or more groups independently selected from OH, oxo, $O(C_1$-$C_6$-alkyl), CN, F, $NH_2$, NH($C_1$-$C_6$-alkyl), N($C_1$-$C_6$-alkyl)$_2$, cyclopropyl, phenyl, imidazolyl, piperidinyl, pyrrolidinyl, morpholinyl, tetrahydrofuranyl, oxetanyl or tetrahydropyranyl,
or $R^5$ and $R^6$ together with the nitrogen to which they are attached form a 4-7 membered heterocyclic ring optionally substituted with one or more groups independently selected from OH, halogen, oxo, $CF_3$, $CH_2CF_3$, $CH_2CH_2OH$, $O(C_1$-$C_3$ alkyl), C(=O)$CH_3$, $NH_2$, NHMe, N(Me)$_2$, S(O)$_2CH_3$, cyclopropylmethyl and $C_1$-$C_3$ alkyl, or
$R^c$ is hydrogen and $R^d$ and $R^6$ together with the atoms to which they are attached form a 4 to 6 membered heterocyclic ring having one nitrogen atom;
$R^a$ and $R^b$ are H,
or $R^a$ is H, and $R^b$ and $R^6$ together with the atoms to which they are attached form a 5-6 membered heterocyclic ring having one or two ring nitrogen atoms;
$R^c$ and $R^d$ are H or Me,
or $R^c$ and $R^d$ together with the atom to which they are attached from a cyclopropyl ring;

each R$^e$ is independently halogen, C$_1$-C$_6$-alkyl, C$_3$-C$_6$-cycloalkyl, O—(C$_1$-C$_6$-alkyl), CF$_3$, OCF$_3$, S(C$_1$-C$_6$-alkyl), CN, OCH$_2$-phenyl, NH$_2$, NO$_2$, N—(C$_1$-C$_6$-alkyl)$_2$, piperidine, pyrrolidine, CH$_2$F, CHF$_2$, OCH$_2$F, OCHF$_2$, OH, SO$_2$(C$_1$-C$_6$-alkyl), C(O)NH$_2$, C(O)NH(C$_1$-C$_6$-alkyl), and C(O)N(C$_1$-C$_6$-alkyl)$_2$;

m and n are independently 0, 1, 2 or 3 with the proviso that (m+n) must equal 2, 3 or 4; and p is 0 or 1.

2. The method of claim 1 wherein:
R$^1$ and R$^{1a}$ are independently selected from H, Me, Et, vinyl, CF$_3$, CHF$_2$ or CH$_2$F;
R$^2$ is H, OH, OMe or F;
R$^{2a}$ is H, Me or F;
R$^3$ is H, Me, Et, or CF$_3$;
A is

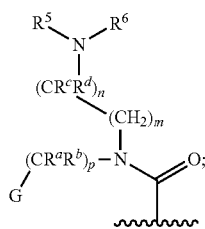

G is phenyl optionally substituted by one to four R$^e$ groups or a 5-6 membered heteroaryl optionally substituted by a halogen;

R$^5$ and R$^6$ are independently H, OCH$_3$, C$_3$-C$_6$-cycloalkyl optionally substituted with F, OH, C$_1$-C$_3$ alkyl or O(C$_1$-C$_3$ alkyl), 4-6 membered heterocycle optionally substituted with F, OH, C$_1$-C$_3$ alkyl, cyclopropylmethyl or C(=O)(C$_1$-C$_3$ alkyl), or C$_1$-C$_6$-alkyl optionally substituted with one or more groups independently selected from OH, oxo, O(C$_1$-C$_6$-alkyl), CN, F, NH$_2$, NH(C$_1$-C$_6$-alkyl), N(C$_1$-C$_6$-alkyl)$_2$, cyclopropyl, phenyl, imidazolyl, piperidinyl, pyrrolidinyl, morpholinyl, tetrahydrofuranyl, oxetanyl or tetrahydropyranyl,
or R$^5$ and R$^6$ together with the nitrogen to which they are attached form a 4-7 membered heterocyclic ring optionally substituted with one or more groups independently selected from OH, halogen, oxo, CF$_3$, CH$_2$CF$_3$, CH$_2$CH$_2$OH, O(C$_1$-C$_3$ alkyl), C(=O)CH$_3$, NH$_2$, NHMe, N(Me)$_2$, S(O)$_2$CH$_3$, cyclopropylmethyl and C$_1$-C$_3$ alkyl;
R$^a$ and R$^b$ are H,
or R$^a$ is H, and R$^b$ and R$^6$ together with the atoms to which they are attached form a 5-6 membered heterocyclic ring having one or two ring nitrogen atoms;
R$_c$ and R$^d$ are H or Me,
or R$^c$ and R$^d$ together with the atom to which they are attached from a cyclopropyl ring;
each R$^e$ is independently halogen, C$_1$-C$_6$-alkyl, C$_3$-C$_6$-cycloalkyl, O—(C$_1$-C$_6$-alkyl), CF$_3$, OCF$_3$, S(C$_1$-C$_6$-alkyl), CN, OCH$_2$-phenyl, NH$_2$, NO$_2$, NH-(C$_1$-C$_6$-alkyl), N—(C$_1$-C$_6$-alkyl)$_2$, piperidine, pyrrolidine, CH$_2$F, CHF$_2$, OCH$_2$F, OCHF$_2$, OH, SO$_2$(C$_1$-C$_6$-alkyl), C(O)NH$_2$, C(O)NH(C$_1$-C$_6$-alkyl), and C(O)N(C$_1$-C$_6$-alkyl)$_2$;

m and n are independently 0, 1 or 2, with the proviso that (m+n) must equal 2, 3 or 4; and p is 0 or 1.

3. The method of claim 1 wherein R$^3$ is H.
4. The method of claim 1 wherein R$^3$ is methyl.
5. The method of claim 4, wherein said methyl is optionally in the (S) configuration.
6. The method of claim 1 wherein R$^3$ is ethyl.
7. The method of claim 1 wherein R$^1$ is methyl.
8. The method of claim 7, wherein said methyl is optionally in the (R) configuration.
9. The method of claim 1 wherein R$^1$ is hydrogen.
10. The method of claim 1 wherein R$^{1a}$ is hydrogen.
11. The method of claim 1 wherein R$^{1a}$ is methyl.
12. The method of claim 1 wherein R$^2$ is H.
13. The method of claim 1 wherein R$^2$ is F.
14. The method of claim 1 wherein R$^2$ is OH.
15. The method of claim 1 wherein R$^{2a}$ is H.
16. The method of claim 1 wherein R$^{2a}$ is F.
17. The method of claim 1 wherein G is phenyl optionally substituted with one to four R$^e$ groups.
18. The method of claim 17, wherein G is phenyl optionally substituted with one to four groups independently selected from F, Cl, Br, I, methyl, ethyl, isopropyl, tert-butyl, cyclopropyl, CN, CF$_3$, OMe, OEt, OCF$_3$, NO$_2$, SMe and OCH$_2$Ph.
19. The method of claim 18, wherein G is 4-chlorophenyl, 4-fluorophenyl, 4-bromophenyl, 4-iodophenyl, 4-trifluoromethylphenyl, 4-trifluormethoxyphenyl, 4-thiomethylphenyl, 3-fluoro-4-chlorophenyl, 2,4-dichlorophenyl or 3,4-dichlorophenyl.
20. The method of claim 1, wherein G is a 5-6 membered monocyclic heteroaryl optionally substituted by one or more halogens.
21. The method of claim 20, wherein G is:

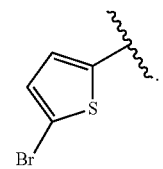 [SMILES: *c1ccc(Br)s1]

22. The method of claim 1 wherein R$^a$ is H.
23. The method of claim 1 wherein R$^b$ is H.
24. The method of claim 1 wherein R$^c$ is H.
25. The method of claim 1 wherein R$^d$ is H.
26. The method of claim 1 wherein R$^5$ is H or ethyl.
27. The method of claim 1 wherein R$^6$ is H or ethyl.
28. The method of claim 1 wherein m is 1 and n is 1.
29. The method of claim 1 wherein p is 0.
30. The method of claims 29, wherein A is:

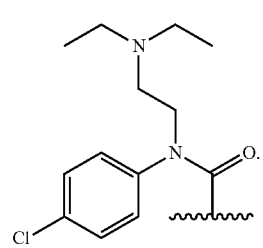 [SMILES: *C(=O)N(CCN(CC)CC)c1ccc(Cl)cc1]

31. The method of claim 1 wherein p is 1.
32. The method of claim 31, wherein A is:

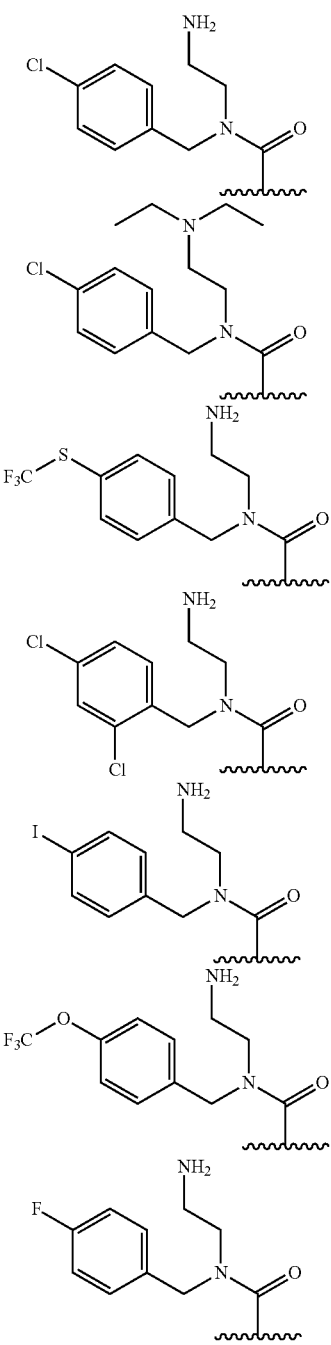
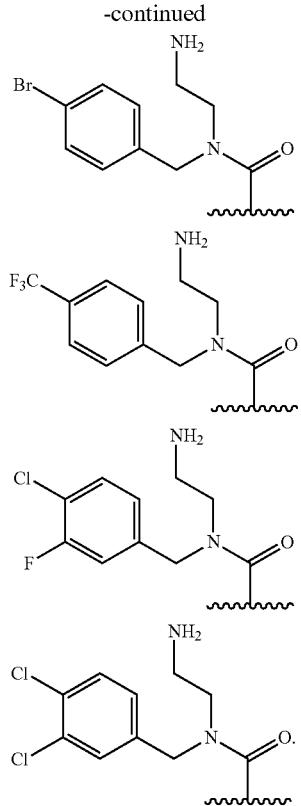
33. The method of claim 31, wherein A is:
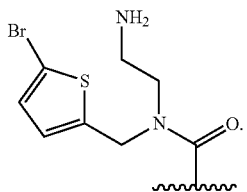 [SMILES: *C(=O)N(CCN)Cc1ccc(Br)s1]
34. The method of claim 1, wherein m is 0, $R^c$ is hydrogen, and $R^d$ and $R^6$ together with the atoms to which they are attached form a 4 to 6 membered heterocyclic ring having one nitrogen atom.
35. The method of claim 34, wherein n is 1 and q is 1, n is 1 and q is 2, or n is 2 and q is 2.
* * * * *

UNITED STATES PATENT AND TRADEMARK OFFICE
CERTIFICATE OF CORRECTION

PATENT NO.        : 8,846,683 B2                                     Page 1 of 1
APPLICATION NO.   : 13/753008
DATED             : September 30, 2014
INVENTOR(S)       : Bencsik et al.

It is certified that error appears in the above-identified patent and that said Letters Patent is hereby corrected as shown below:

In the Claims

In Claim 1, Column 59, Line 3-4:

Replace:

$NO_2$, N—$(C_1-C_6\text{-alkyl})_2$,

With:

$NO_2$, NH—$(C_1-C_6\text{-alkyl})$, N-$(C_1-C_6\text{-alkyl})_2$,

In Claim 2, Column 59, Line 53:

Replace:

$R_c$

With:

$R^c$

Signed and Sealed this
Twelfth Day of May, 2015

Michelle K. Lee
*Director of the United States Patent and Trademark Office*